(12) United States Patent
Cowart et al.

(10) Patent No.: US 8,026,240 B2
(45) Date of Patent: Sep. 27, 2011

(54) OCTAHYDRO-PYRROLO[3,4-B]PYRROLE N-OXIDES

(75) Inventors: Marlon D. Cowart, Round Lake Beach, IL (US); Kennan C. Marsh, Lake Forest, IL (US); Huaqing Liu, Buffalo Grove, IL (US); Jae Y. Lee, Buffalo Grove, IL (US); Maria G. Beconi, Lake Forest, IL (US); Jill M. Wetter, Beach Park, IL (US); Lawrence A. Black, Libertyville, IL (US); Thomas C. Custer, Lake Bluff, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/208,604

(22) Filed: Sep. 11, 2008

(65) Prior Publication Data

US 2009/0105267 A1    Apr. 23, 2009

Related U.S. Application Data

(60) Provisional application No. 60/971,402, filed on Sep. 11, 2007.

(51) Int. Cl.
| | |
|---|---|
| C07D 401/14 | (2006.01) |
| C07D 247/02 | (2006.01) |
| C07D 237/14 | (2006.01) |
| A61K 31/501 | (2006.01) |
| A61P 3/04 | (2006.01) |
| A61P 11/06 | (2006.01) |
| A61P 27/14 | (2006.01) |

(52) U.S. Cl. ............... 514/252.03; 514/252.06; 544/238
(58) Field of Classification Search .................. 544/238; 514/252.03, 252.06
See application file for complete search history.

(56) References Cited

U.S. PATENT DOCUMENTS

| 5,071,999 | A | 12/1991 | Schenke et al. |
|---|---|---|---|
| 7,462,599 | B2 | 12/2008 | Schilling et al. |
| 2004/0092521 | A1 | 5/2004 | Altenbach et al. |
| 2005/0101602 | A1 | 5/2005 | Basha et al. |
| 2005/0245543 | A1 | 11/2005 | Howard et al. |
| 2006/0019998 | A1 | 1/2006 | Wager et al. |
| 2008/0221093 | A1 | 9/2008 | Gege et al. |

FOREIGN PATENT DOCUMENTS

| DE | 3231088 | 2/1990 |
|---|---|---|
| EP | 0393424 | 9/1995 |
| EP | 0350733 | 8/1997 |
| WO | 9635691 | 11/1996 |
| WO | 00/24719 | 5/2000 |
| WO | 01/66534 | 9/2001 |
| WO | 01/81347 | 11/2001 |
| WO | 0206223 | 1/2002 |
| WO | 0206278 | 1/2002 |
| WO | 0240461 | 5/2002 |
| WO | 02070523 | 9/2002 |
| WO | 02072093 | 9/2002 |
| WO | 2004092173 | 10/2004 |
| WO | 2004097408 | 11/2004 |
| WO | 2005/054194 | 6/2005 |
| WO | 2005056056 | 6/2005 |
| WO | 2005075479 | 8/2005 |
| WO | 2006/018280 | 2/2006 |
| WO | 2007007069 | 1/2007 |
| WO | 2007027734 | 3/2007 |
| WO | 2007093363 | 8/2007 |
| WO | 2007093364 | 8/2007 |
| WO | 2007/100990 | 9/2007 |
| WO | 2007100990 | 9/2007 |
| WO | 2007110868 | 10/2007 |
| WO | 2008005338 | 1/2008 |
| WO | 2008014240 | 1/2008 |
| WO | 2008023239 | 2/2008 |
| WO | 2008024978 | 2/2008 |
| WO | 2008041090 | 4/2008 |
| WO | 2008059238 | 5/2008 |
| WO | 2008153958 | 12/2008 |

OTHER PUBLICATIONS

Rozniecki, et al., Pharmacology & Experimental Therapeutics, vol. 290, #3, 1427-1435, Sep. 1999.*
Wikipedia, Histamine H3 receptor, last modified Sep. 27, 2009, downloaded Sep. 28, 2009.*
Abdel-Magid, et al., Journal of Organic Chemistry, Reductive Amination of Aldehydes and Ketones with Sodium Triacetoxyborohydride. Studies on Direct and Indirect Reductive Amination Proceduresvol. 61, pp. 3849-3862 (1996).
Aranyos, A., et al., "Novel Electron-Rich Bulky Phosphine Ligands Facilitate the Palladium-Catalyzed Preparation of Diaryl Esthers", Journal of American Chemical Society, vol. 121, pp. 4369-4378, 1999.
Arrang, J.-M., et al., "Auto-inhibition of brain histamine release mediated by a novel class ($H_3$) of histamine receptor", Nature, vol. 302, pp. 832-837, 1983.
Arrang, J.-M., et al., "Highly potent and selective ligands for histamine $H_3$-receptors", Nature, vol. 327, pp. 117-123, 1987.
Barbier, A.J., et al., "Acute wake-promoting actions of JNJ-5207852, a novel, diamine-based $H_3$ antagonist", British Journal of Pharmacology, vol. 143, pp. 649-661, 2004.
Bates, R., et al., "High-Yield Benzyne Synthesis of Diaryl Ethers", Journal of Organic Chemistry, vol. 47, pp. 4374-4376, 1982.
Bernaerts, P., et al., "Histamine $H_3$ antagonist thioperamide dose-dependently enhances memory consolidation and reverses amnesia induced by dizocilpine or scopolamine in a one-trial inhibitory avoidance task in mice", Behavioural Brain Research, vol. 154, pp. 211-219, 2004.

(Continued)

Primary Examiner — James O Wilson
Assistant Examiner — Cecilia M Jaisle
(74) Attorney, Agent, or Firm — Portia Chen

(57) ABSTRACT

The invention relates to octahydro-pyrrolo[3,4-b]pyrrole N-oxides as prodrugs of CNS-active compounds, compositions comprising such compounds, methods for making the compounds, salts, and polymorphs, and methods of treating conditions and disorders using such compounds and compositions. Octahydro-pyrrolo[3,4-b]pyrrole N-oxides of formula (I) are prodrugs of histamine-3 antagonists, and are useful in treating conditions or disorders prevented by or ameliorated by histamine-3 receptor ligands. Octahydro-pyrrolo[3,4-b]pyrrole N-oxide compounds, methods for using such compounds, compositions for making them, and processes for preparing such compounds are disclosed herein.

7 Claims, No Drawings

OTHER PUBLICATIONS

Bjenning, C., et al., "Peripherally administered ciproxifan elevates hypothalamic histamine levels and potently reduces food intake in the Sprague Dawley rat", Abstracts, International Sendai Histamine Symposium, Sendai, Japan, #P39, pp. 449-452, Nov. 2000.

Black, W.C., et al., "2, 3-Diarylcyclopentenones as Orally Active, Highly Selective Cyclooxygenase-2 Inhibitors", Journal of Medicinal Chemistry, vol. 42, p. 1274-1281, 1999.

Browman, K.E., et al., "Enhancement of prepulse inhibition of startle in mice by the $H_3$ receptor antagonists thioperamide and ciproxifan", Behavioural Brain Research, vol. 153, No. 1, pp. 69-76, 2004.

Burns, et al., "PET ligands for assessing receptor occupancy in vivo", Annual Reports in Medicinal Chemistry, vol. 36, pp. 267-276, 2001.

Burns, et al., "Positron emission tomography neuroreceptor imaging as a tool in drug discovery, research and development", Current Opinion in Chemical Biology, vol. 3, No. 4, pp. 388-394, 1999.

Carroll, F.I., et al., "Synthesis, Nicotinic Acetylcholine Receptor Binding, and Antinociceptive Properties of 2-exo-2-(2'-Substituted 5'-pyridinyl)-7-azabicyclo[2.2.1]heptanes. Epibatidine Analogues", Journal of Medicinal Chemistry, pp. 2229-2237, 2001.

Chávez, et al., "Histamine ($H_3$) receptors modulate the excitatory amino acid receptor response of the vestibular afferents", Brain Research, vol. 1064, pp. 1-9, 2005.

Chen, et al., "Effects of histamine on MK-801-induced memory deficits in radial maze performance in rats", Brain Research, vol. 839, pp. 186-189, 1999.

Chen, Z., et al., "Pharmacological effects of carcinine on histaminergic neurons in the brain", British Journal of Pharmacology, vol. 143, pp. 573-580, 2004.

Clapham, J., et al., "Thioperamide, the selective histamine $H_3$ receptor antagonist, attenuates stimulant-induced locomotor activity in the mouse", European Journal of Pharmacology, vol. 259, No. 2, pp. 107-114, 1994.

Cowart, et al., "4-(2-[2-(2(R)-Methylpyrrolidin-1-yl)ethyl]benzofuran-5-yl)benzonitrile and Related 2-Aminoethylbenzofuran H3 Receptor Antagonists Potently Enhance Cognition and Attention", Journal of Medicinal Chemistry, vol. 48, pp. 38-55, 2005.

de Almeida, et al., "Memory Facilitation by Histamine", Archives of Int Pharmacodyn, vol. 283, pp. 193-198, 1986.

Delaunois, A.A., et al., "Modulation of acetylcholine, capsaicin and substance P effects by histamine $H_3$ receptors in isolated perfused rabbit lungs", European Journal of Pharmacology, vol. 277, pp. 243-250, 1995.

Dimitriadou, et al., "Functional relationship between mast cells and C-sensitive nerve fibres evidenced by histamine $H_3$-receptor modulation in rat lung and spleen", Clinical Science, vol. 87, pp. 151-163, 1994.

Duméry, V., et al., "Development of amygdaloid cholinergic mediation of passive avoidance learning in the rat", Experimental Brain Research, vol. 67, pp. 61-69, 1987.

Dvorak, C., et al., "4-Phenoxypiperidines: Potent, Conformationally, Restricted, Non-Imidazole Histamine $H_3$ Antagonists", Journal of Medicinal Chemistry, vol. 48, pp. 2229-2238, 2005.

Esbenshade, T.A., et al., "Pharmacological Properties of ABT-239 [4-(2-{2-[(2R)-2-Methylpyrrolidinyl]ethyl}-benzofuran-5-yl)benzonitrile]: I. Potent and Selective Histamine $H_3$ Receptor Antagonist with Drug-Like Properties", Journal of Pharmacology and Experimental Therapeutics, vol. 313, pp. 165-175, 2005.

Esbenshade, T.A., et al., "Pharmacological and behavioral properties of A-349821, selective and potent human histamine H3 receptor antagonist", Biochemical Pharmacology, vol. 68, pp. 933-945, 2004.

Fitzsimons, C.H., et al., "Histamine receptors signaling in epidermal tumor cell lines with H-ras gene alterations", Inflammation Research, vol. 47 (Suppl. 1), pp. S50-S51, 1998.

Fox, G.B., et al., "Effects of histamine $H_3$ receptor ligands GT-2331 and ciproxifan in a repeated acquisition avoidance response in the spontaneously hypertensive rat pup", Behavioural Brain Research, vol. 131, pp. 151-161, 2002.

Fox, G.B., et al., "Two Novel and Selective Nonimidazole H3 Receptor Antagonists A-304121 and A-317920: II. In Vivo Behavioral and Neurophysiological Characterization", Journal of Pharmacology and Experimental Therapeutics, vol. 305, pp. 897-908, 2003.

Fox, G.B., "Identification of novel $H_3$ receptor ($H_3R$) antagonists with cognition enhancing properties in rats", Inflammation Research, vol. 52, pp. S31-S32, 2003.

Fox, G.B., et al., "Pharmacological Properties of ABT-239 [4-(2-{2-[(2R)-2-Methylpyrrolidinyl]ethyl}-benzofuran-5-yl)benzonitrile]: II. Neurophysiological Characterization and Broad Preclinical Efficacy in Cognition and Schizophrenia of a Potent and Selective Histamine $H_3$ Receptor Antagonist", Journal of Pharmacology and Experimental Therapeutics, vol. 313, No. 1, pp. 176-190, 2005.

Furniss, et al., "Vogel's Textbook of Practical Organic Chemistry", $5^{th}$ Ed., Table of Contents, 1989.

Glase, S.A., et al., "Attention deficit hyperactivity disorder: Pathophysiology and design of new treatments", Annual Reports in Medicinal Chemistry, vol. 37, pp. 11-20, 2002.

Greene, T.W., et al., Protective Groups in Organic Synthesis, $3^{rd}$ Ed., John Wiley & Sons, New York, 1999.

Haas, H.L., et al., "Subcortical modulation of synaptic plasticity in the hippocampus", Behavioural Brain Research, vol. 66, pp. 41-44, 1995.

Haga, N., et al., "Mechanisms of the Photochemical Rearrangement of Diphenyl Ethers", Journal of Organic Chemistry, vol. 61, pp. 735-745, 1996.

Halpern, M.T., "GT-2331", Current Opinion in CPNS Investigational Drugs, vol. 1, No. 4, pp. 524-527, 1999.

Hancock, A.A., "Antiobesity effects of A-331440, a novel non-imidazole histamine $H_3$ receptor antagonist", European Journal of Pharmacology, vol. 487, pp. 183-197, 2004.

Hancock, A.A., et al., "Histamine $H_3$ antagonists in models of obesity", Inflammatory Research, vol. 53, Supplement 1, S47-S48, 2004.

Harada, C., et al., "Inhibitory effect of iodophenpropit, a selective histamine $H_3$ antagonist, on amygdaloid kindled seizures", Brain Research Bulletin, vol. 63, No. 2, pp. 143-146, 2004.

Hartwig, J.F., et al., "Room-Temperature Palladium-Catalyzed Amination of Aryl Bromides and Chlorides and Extended Scope of Aromatic C-N Bond Formation with a Commercial Ligand", Journal of Organic Chemistry, vol. 64, No. 15, pp. 5575-5580, 1999.

Hartwig, J.F., et al., "Transition Metal Catalyzed Synthesis of Arylamines and Aryl Ethers from Aryl Halides and Triflates: Scope and Mechanism", Angewandte Chemie International Edition, vol. 37, pp. 2046-2067, 1998.

Hietala, J.F., "Ligand-receptor interactions as studied by PET: implications for drug development", Annals of Medicine (Helsinki), vol. 31, No. 6, pp. 438-443, 1999.

Higuchi, T., et al., Pro-drugs as Novel Delivery Systems, vol. 14, A.C.S. Symposium Series, 1975.

Hriscu, A., "Experimental evaluation of the analgesic efficacy of some antihistamines as proof of the histaminergic receptor involvement in pain", Famacia, vol. 49, No. 2, pp. 23-30, 76, 2001.

Huang, Y.-W., et al., "Effect of the histamine $H_3$-antagonist clobenpropit on spatial memory deficits induced by MK-801 as evaluated by radial maze in Sprague-Dawley rats", Behavioural Brain Research, vol. 151, pp. 287-293, 2004.

Huck, B.R., et al., "The identification of pyrimidine-diazabicyclo[3.3.0]octane derivatives as 5-$Ht_{2C}$ receptor agonists", Bioorg. & Medic. Chem. Ltrs., 16(11):2891-2894 (2006).

Ishiyama, T., et al., "Synthesis of pinacol arylboronates via cross-coupling reaction of bis(pinacolato)diboron with chloroarenes catalyzed by palladium(0)-tricyclohexylphosphine complexes", Tetrahedron, vol. 57, pp. 9813-9816, 2001.

Itoh, E., et al., "Thioperamide, a Histamine $H_3$ Receptor Antagonist, Powerfully Suppresses Peptide YY-Induced Food Intake in Rats", Biological Psychiatry, vol. 45, No. 4, pp. 475-481, 1999.

IUPAC, 1974 Recommendations for Section E, Fundamental Stereochemistry, Comm on Nomenclature of Org. Chem., Pure Appl Chem., vol. 45, pp. 13-30, 1976.

Kamei, C., et al., "Participation of Histamine in the Step-Through Active Avoidance Response and its Inhibition by H1-Blockers", Japan Journal of Pharmacology, vol. 57, pp. 473-482, 1991.

Kamei, C., et al., "Influence of certain H1-blockers on the step-through active avoidance response in rats", Psychopharmacology, vol. 102, pp. 312-318, 1990.

Kiyomori, A., et al., "An Efficient Copper-Catalyzed Coupling of Aryl Halides with Imidazoles", Tetrahedron Letters, vol. 40, pp. 2657-2660, 1999.

Klapars, A., et al., "A General and Efficient Copper Catalyst for the Amidation of Aryl Halides and the N-Arylation of Nitrogen Heterocycles", Journal of the American Chemistry Society, vol. 123, pp. 7727-7729, 2001.

Komater, V.A., et al., "$H_3$ receptor blockade by thioperamide enhances cognition in rats without inducing locomotor sensitization", Psychopharmacology, vol. 167, pp. 363-372, 2003.

Krueger, et al., Journal of Pharmacology and Experimental Therapeutics vol. 314, pp. 271-281 (2005).

Kuwabe, S.-I., et al., "Palladium-Catalyzed Intramolecular C-O Bond Formation", Journal of the American Chemical Society, vol. 123, pp. 12202-12206, 2001.

Kwong, F.Y., et al., "Copper-Catalyzed Coupling of Alkylamines and Aryl Iodides: An Efficient System Even in an Air Atmosphere", Organic Letters, vol. 4, No. 4, pp. 581-584, 2002.

Lamberti, C., et al., "Antidepressant-like effects of endogenous histamine and of two histamine $H_1$ receptor agonists in the mouse forced swim test", British Journal of Pharmacology, vol. 123, pp. 1331-1336, 1998.

Letsinger, R.L., et al., "Organoboron Compounds. IX. 8-Quinolineboronic Acid, its Preparation Influence on Reactions of Chlorohydrins", Journal of the American Chemical Society, vol. 81, pp. 498-501, 1959.

Leurs, R., et al., Ed., "The History of $H_3$ Receptor: a Target for New Drugs", Elsevier, 1998.

Leurs, R., et al., "The histamine $H_3$-receptor: a target for developing new drugs", Progress in Drug Research, vol. 39, p. 127-165, 1992.

Leurs, R., et al., "The histamine $H_3$-receptor: From gene cloning to $H_3$ receptor drugs", Native Reviews Drug Discovery, vol. 4, pp. 107-120, 2005.

Leurs, R., et al., "The medicinal chemistry and therapeutic potential of ligands of the histamine $H_3$ receptor", Progress in Drug Research, vol. 45, pp. 107-165, 1995.

Li, G.Y., "The First Phosphine Oxide Ligand Precursors for Transition Metal Catalyzed Cross-Coupling Reactions: C-C, C-N, and C-S Bond Formation on Unactivated Aryl Chlorides", Angewandte Chemie International Edition, vol. 40, pp. 1513-1516, 2001.

Li, G.Y., et al., "Highly Active, Air-Stable Versatile Palladium Catalysts for the C-C, C-N, and C-S Bond Formations via Cross-Coupling Reactions of Aryl Chlorides", Journal of Organic Chemistry, vol. 66, pp. 8677-8681, 2001.

Ligneau, X., et al., "Neurochemical and Behavioral Effects of Ciproxifan, a Potent Histamine $H_3$-Receptor Antagonist", Journal of Pharmacology and Experimental Therapeutics, vol. 287, No. 2, pp. 658-666, 1998.

Lin, J.-S., et al., "Involvement of histaminergic neurons in arousal mechanisms demonstrated with $H_3$-Receptor ligands in the cat", Brain Res, vol. 523, pp. 325-330, 1990.

Liu, G., et al., "Novel p-Arylthio Cinnamides as Antagonists of Leukocyte Function-Associated Antigen-1/Intracellular Adhesion Molecule-1 Interaction. 2. Mechanism of Inhibition and Structure-Based Improvement of Pharmaceutical Properties", Journal of Medicinal Chemistry, vol. 44, pp. 1202-1210, 2001.

Lozada, A.F., et al., "Plasticity of histamine $H_3$ receptor expression and binding in the vestibular nuclei after labyrinthectomy in rat", BioMedCentral Neuroscience, 5:32, pp. 1-9, 2004.

Malmberg-Aiello, P., et al., "Role of histamine in rodent antinociception", British Journal of Pharmacology, vol. 111, No. 4, pp. 1269-1279, 1994.

Malmlöf, K., et al., "Influence of a selective histamine $H_3$ receptor antagonist on hypothalamic neural activity, food intake and body weight", International J of Obesity, vol. 29, pp. 1402-1412, 2005.

Mann, G., et al., "Palladium-Catalyzed Formation of Diaryl Ethers from Aryl Bromides. Electron Poor Phosphines Enhance Reaction Yields", Tetrahedron Letters, vol. 38, No. 46, pp. 8005-8008, 1997.

Marcoux, J.-F., et al., "A General Copper-Catalyzed Synthesis of Diaryl Ethers", Journal of the American Chemical Society, vol. 119, pp. 10539-10540, 1997.

Mazurkiewicz-Kwilecki, I.M., et al., "Changes in the regional brain histamine and histidine levels in postmortem brains of Alzheimer patients", Canadian Journal of Physiology and Pharmacology, vol. 67, pp. 75-78, 1989.

McLeod, R.L, et al., "Combined Histamine $H_1$ and $H_3$ Receptor Blockade Produces Nasal Decongestion in an Experimental Model of Nasal Congestion", American Journal of Rhinology, vol. 13, No. 5, pp. 391-399, 1999.

McLeod, R.L., et al., "Histamine $H_3$ Antagonists", Progress in Respiratory Research, vol. 31, pp. 133-136, 2001.

Meguro, K.-I., et al., "Effects of Thioperamide, a Histamine $H_3$ Antagonist, on the Step-Through Passive Avoidance Response and Histidine Decarboxylase Activity in Senescence-Accelerated Mice", Pharmacology Biochemistry and Behavior, vol. 50, No. 3, p. 321-325, 1995.

Miyaura, N., et al ., "Palladium-Catalyzed Cross-Coupling Reactions of Organoboron Compounds", Chem Review, vol. 95, p. 2457-2483, 1995.

Monti, J.M., et al., "Effects of selective activation or blockade of the Histamine $H_3$ receptor on sleep and wakefulness", European Journal of Pharmacology, vol. 205, p. 283-287, 1991.

Monti, J.M., et al., "Sleep and Waking During Acute Histamine $H_3$ Agonist BP 2.94 or $H_3$ Antagonist Carboperamide (MR 16155) Administration in Rats", Neuropsychopharmacology, vol. 15, pp. 31-35, 1996.

Morisset, S., et al., "Atypical Neuroleptics Enhance Histamine Turnover in Brain Via 5-Hydroxytryptamine.sub.2A Receptor Blockade" Journal of Pharmacology and Experimental Therapeutics, vol. 288, No. 2, pp. 590-596, 1999.

Murakami, K., et al., "AQ-0145, A newly developed histamine", Methods and Findings in Experimental and Clinical Pharmacology, vol. 17 (C), pp. 70-73, 1995.

Olivera, R., et al., "Dibenzoxepino[4,5-d]pyrazoles: a facile approach via the Ullmann-ether reaction", Tetrahedron Letters, vol. 41, pp. 4353-4356, 2000.

O'Neill, B.T., et al., "Pharmacological Evaluation of an In Vivo Model of Vestibular Dysfunction in the Rat", Methods and Findings in Clinical Pharmacology, vol. 21, No. 4, pp. 285-289, 1999.

O'Neill, B.T., et al., "Total Synthesis of (±)-Cytisine", Organic Letters, vol. 2, No. 26, p. 4201-4206, 2000.

Onodera, K., et al., "Improvement by FUB 181, a novel histamine $H_3$-receptor antagonist, of learning and memory in the elevated plus-maze test in mice", Naunyn-Schmiedebergs' Arch Pharmacol, vol. 357, pp. 508-513, 1998.

Onodera, K., et al., "Neuropharmacology of the histaminergic neuron system in the brain and its relationship with behavioral disorders", Progress in Neurobiology, vol. 42, p. 685-702, 1994.

Palomo, C., et al., "Phosphazene bases for the preparation of biaryl thioethers from aryl iodides and arenethiols", Tetrahedron Letters, vol. 41, 1283-1286, 2000.

Palucki, M., et al., "Palladium-Catalyzed Intermolecular Carbon-Oxygen Bond Formation: A New Synthesis of Aryl Ethers", Journal of the American Chemical Society, vol. 119, pp. 3395-3396, 1997.

Pan, J.B., et al., "Histaminergic Ligands Attentuate Barrel Rotation in Rats Following Unilateral Labyrinthectomy", Methods and Findings in Clinical Pharmacology, vol. 20, No. 9, pp. 771-777, 1998.

Panula, P., et al., "Neuronal Histamine Deficit in Alzheimer's Disease", Neuroscience, vol. 82, No. 4, pp. 993-997, 1998.

Passani, M.B., et al., "Central histaminergic system and cognition", Neuroscience and Biobehavioral Reviews, vol. 24, pp. 107-113, 2000.

Pérez-Garcia, C., et al., "Effects of histamine $H_3$ receptor ligands in experimental models of anxiety and depression", Psychopharmacology (Berlin), vol. 142, No. 2, pp. 215-220, 1999.

Prast, H., et al., "Histaminergic neurons facilitate social memory in rats", Brain Research, vol. 734, pp. 316-318, 1996.

Poste G., et al., Prescott, Ed., Methods in Cell Biology, vol. XIV, Academic Press, New York, NY, pp. 33 et seq., 1976.

Pu, Y.-M., et al., "An efficient copper-catalyzed N-arylation of pyridazinones with a structurally well-defined copper complex", Tetrahedron Letters, vol. 47, No. 2, pp. 149-153, 2006.

Roche, E.B., ed., Bioreversible Carriers in Drug Design, American Pharmaceutical Association and Pergamon Press, 1987.

Rodrigues, A.A., et al., "Interaction of clozapine with the histamine $H_3$ receptor in rat brain", British Journal of Pharmacology, vol. 114, pp. 1523-1524. 1995.

Sakai, N., et al., "Effects of Thioperamide, a Histamine $H_3$ Receptor Antagonist, On Locomotor Activity and Brain Histamine Content in Mast Cell-Deficient W/W v Mice", Life Sciences, vol. 48, pp. 2397-2404, 1991.

Sakata, T., et al., "Hypothalamic neuronal histamine modulates ad libitum feeding by rats", Brain research, vol. 537 (1-2), pp. 303-306, 1990.

Sánchez-Lemus, E., et al., "Histamine $H_3$ receptor activation inhibits dopamine $D_1$ receptor-induced cAMP accumulation in rat striatal slices", Neuroscience Letters, vol. 364, pp. 179-184, 2004.

Satoh, T., et al., "Regioselective Arylation Reactions of Biphenyl-2-ols, Naphthols, and Benzylic Compounds with Aryl Hallides under Palladium Catalysis", Bulletin of the Chemical Society of Japan., vol. 71, pp. 2239-2246, 1998.

Schopfer, U., et al., "A general palladium-catalyzed synthesis of aromatic and heteroaromatic thioethers", Tetrahedron, vol. 57, pp. 3069-3074, 2001.

Schwartz, J.-C., et al., "Histamine", Psychopharmacology: The Fourth Generation of Progress, Raven Press, Ltd., New York, 1995.

Schweitzer, J.B., et al., "Drugs under investigation for attention-deficit hyperactivity disorder", Current Opinion in Investigational Drugs, vol. 3, No. 8, pp. 1207-1211, 2002.

Shaywitz, et al., "Dopaminergic but not noradrenergic mediation of hyperactivity and performance deficits in the developing rat pup", Psychopharmacology, vol. 82, pp. 73-77, 1984.

Sindkhedkar, M.D., et al., "Aromatic Interactions of the Synthesis and Conformation of Two Collapsible Tetracationic Cyclophanes", Tetrahedron, vol. 57, p. 2991-2996, 2000.

Stella, Expert Opinion on Ther. Patents, "Prodrugs as Therapeutics", 14:277-280 (2004).

Sugahara, M., et al., "A Facile Copper-Catalyzed Ulmann Condensation: N-Arylation of Heterocyclic Compounds Containing an -NHCO- Moicty", Chemical and Pharmaceutical Bulletin, vol. 45, No. 4, pp. 719-721, 1997.

Szelag, A., "Role of histamine $H_3$-receptors in the proliferation of neoplastic cells in vitro", Polish Medical Science Monitor, vol. 4, No. 5, pp. 747-755, 1998.

Takagi, et al., "Iridium-catalyzed C—H coupling reaction of heteroaromatic compounds with bis(pinacolato)diboron: regioselective synthesis of heteroarylboronates", Tetrahedron Letters, vol. 43, pp. 5649-5651, 2002.

Tedford, et al., "Pharmacological Characterization of GT-2016, a Non-Thiourea Containing Histamine $H_3$-Receptor Antagonist: In Vitro and In Vivo Studies", Journal of Pharmacology and Experimental Therapeutics, vol. 275, No. 2, pp. 598-604, 1995.

Tedford, C.E., et al., "Cognition and Locomotor Activity in the Developing Rat: Comparisons of Histamine $H_3$ Receptor Antagonists and ADHD Therapeutics", Soc Neurosci Abstr, vol. 22, p. 22, 1996.

Torraca, K.E., et al., "A High-Yield, General Method for the Catalytic Formation of Oxygen Heterocycles", Journal of the American Chemical Society, vol. 122, No. 51 pp. 12907-12908, 2000.

Torraca, K.E., et al., "An Efficient Intermolecular Palladium-Catalyzed Synthesis of Aryl Ethers", Journal of the American Chemical Society, vol. 123, pp. 10770-10771, 2001.

Tozer, M., et al., "Histamine $H_3$ Receptor Antagonists", Expert Opinion Therapeutic Patents, vol. 10, No. 7, pp. 1045-1055, 2000.

Tsuji, J., Palladium Reagents and Catalysts-Innovations in Organic Synthesis, John Wiley & Sons: New York, 1995.

Vohora, D., et al., "Thioperamide, a Selective Histamine $H_3$ Receptor Antagonist, Protects Against PTZ-Induced Seizures in Mice", Life Sciences, vol. 66, pp. PL 297-301, 2000.

Wada, H., et al., "Is the histaminergic neuron system a regulatory center for whole-brain activity?", Trends in Neuroscience, vol. 14, No. 9, pp. 415-421, 1991.

Wang, Y., et al., "Design and Synthesis of Ether Analogues as Potent and Selective M2 Muscarinic Receptor Antagonists", Bioorganic and Medicinal Chemistry Letters, vol. 11, pp. 891-894, 2001.

Wolfe, J.P., et al., "Rational Development of Practical Catalysts for Aromatic Carbon-Nitrogen Bond Formation", Accounts of Chemical Research, vol. 31, pp. 805-818, 1998.

Wolfe, J.P., et al., "Simple, Efficient Catalyst System for the Palladium-Catalyzed Amination of Aryl Chlorides, Bromides, and Triflates", Journal of Organic Chemistry, vol. 65, pp. 1158-1174, 2000.

Yamamoto, T., et al., "Ullman Condensation Using Copper or Copper Oxide as the Reactant. Arylation of Active Hydrogen Compounds (imides, amides, amines, phenol, benzoic acid, and phenylacetylene)", Canadian Journal of Chemistry, vol. 61, pp. 86-91, 1983.

Yang, B.H., et al., "Palladium-catalyzed amination of aryl halides and sulfonates", Journal of Organometallic Chemistry, vol. 576, pp. 125-146, 1999.

Yates, S.L., et al., "Effects of a novel histamine $H_3$ receptor antagonist, GT2394, on food intake and weight gain in Sprague-Dawley rats", Society for Neuroscience, vol. 102, No. 10, p. 219, 2000.

Yates, S.L., et al., "Identification and Pharmacological Characterization of a Series of New 1H-4-Substituted-Imidazoyl Histamine $H_3$ Receptor Ligands", Journal of Pharmacology and Experimental Therapeutics, vol. 289, pp. 1151-1159, 1999.

Yawata, I., et al., "Role of histaminergic neurons in development of epileptic seizures in EL mice", Molecular Brain Research, vol. 132, pp. 13-17, 2004.

Yokoyama, H., et al., "Effect of thioperamide, a histamine $H_3$ antagonist, on electrically induced convulsions in mice", European Journal of Pharmacology, vol. 234, pp. 129-133, 1993.

Yokoyama, H., et al., "Clobenpropit (VUF-9153), a new histamine $H_3$ receptor antagonist, inhibits electrically induced convulsions in mice", European Journal of Pharmacology, vol. 260, pp. 23-28, 1994.

Yokoyama, H., et al., "Histamine and Seizures: Implications for the Treatment of Epilepsy", CNS Drugs, vol. 5, No. 5, pp. 321-330, 1996.

International Search Report for PCT/US2008/075967 mailed Dec. 15, 2008.

International Search Report for PCT/US2007/062329 mailed Aug. 29, 2007.

Pagliara, et al., J. Med. Chem. Molecular Properties and Pharmacokinetic Behavior of Cetirizine, a Zwitterionic H1-Receptor Antagonist 41:853-863 (1998).

Pu, et al., Organic Process Research and Development, "A Facile and Scaleable Synthesis of ABT-239, A Benzofuranoid H3 Antagonist" 9:45-50 (2005).

Opposition papers received in Ecuadorian counterpart Application No. SP-08-08687 PCT, dated Feb. 5, 2009.

Opposition document received in Costa Rican counterpart Application No. PCT/US2007/0623329; File No. 10287, dated Mar. 13, 2009. (English translation).

Examination Report received from Intellectual Property Office of Singapore in Singapore Patent Application No. 200805587-3, related to PCT/US2007/0623329, dated Sep. 28, 2010.

* cited by examiner

OCTAHYDRO-PYRROLO[3,4-B]PYRROLE N-OXIDES

RELATED APPLICATION INFORMATION

This application claims priority to U.S. Application No. 60/971,402, filed on Sep. 11, 2007, the contents of which are herein incorporated by reference.

BACKGROUND OF THE INVENTION

1. Technical Field

The invention relates to octahydro-pyrrolo[3,4-b]pyrrole N-oxides, compositions comprising such compounds, methods for making the compounds, salts, and polymorphs, and methods of using said compounds as prodrugs for treating conditions and disorders where modulation of histamine-3 ($H_3$) receptor activity is of therapeutic benefit.

2. Description of Related Technology

Histamine is a well-known modulator of neuronal activity. At least four types of histamine receptors have been reported in the literature, typically referred to as histamine-1, histamine-2, histamine-3, and histamine-4. The class of histamine receptor known as the histamine-3 receptor (also sometimes called the histamine $H_3$ receptor or the $H_3$ receptor) is believed to play a role in neurotransmission in the central nervous system.

The histamine-3 ($H_3$) receptor was first pharmacologically characterized on histaminergic nerve terminals (Arrang et al, "Auto-inhibition of Brain Histamine Release Mediated by a Novel Class ($H_3$) of Histamine Receptor", *Nature*, Vol. 302, pp. 832-837 (1983)). The histamine-3 receptor is able to regulate the release of neurotransmitters in the central nervous system and peripheral nervous system, and also in peripheral organs such as the gastrointestinal tract. Histamine-3 ligands have been shown to be able to modulate the release of histamine, dopamine, serotonin, acetylcholine, and other neurotransmitters. The existence of histamine-3 receptors and their established role in modulating neurotransmitter release activity in animal models of disease indicate the utility of histamine-3 ligands for the treatment of disease. This has motivated a search for, and the development of, selective histamine-3 receptor agonists and antagonists (Leurs et al., *Nature Reviews Drug Discovery*, Vol. 4, pp. 107-120 (2005); Arrang et al. "Highly potent and selective ligands for histamine H3-receptors," *Nature*, Vol. 327, pp. 117-123 (1987); Leurs and Timmerman, ed. "The History of $H_3$ Receptor: A Target for New Drugs," *Elsevier* (1998)).

The activity of histamine-3 receptors can be modified or regulated by the administration of histamine-3 receptor ligands. The ligands can demonstrate antagonist, inverse agonist, or partial agonist activity. Histamine-3 receptors have been linked to conditions and disorders related to the central nervous system involving memory, cognition, attention, and other neurological processes, wakefulness, obesity, and also peripheral and systemic activities, such as those involved in asthma and allergic rhinitis. Although various classes of compounds demonstrating histamine-3 receptor-modulating activity exist, it would be beneficial to provide additional compounds that can be incorporated into pharmaceutical compositions useful for therapeutic methods.

Prodrugs are a suitable manner for providing therapeutic compounds. Approximately 5-7% of all commercial drugs worldwide are prodrugs (Stella, *Expert Opinion on Therapeutic Patents*, Vol. 14, pp. 277-280 (2004)). Prodrugs distinguish themselves in one or more significant ways. They are structurally different from the active daughter compound, and they may have distinct physicochemical properties. Prodrugs can therefore be used, for example, to solve drug delivery problems, and in general to overcome some barriers to the utility of the parent drug molecule, for example, they can help bypassing of drug efflux mechanisms, extend and delay drug absorption to extend the period of drug action, and generally improve bioavailability and biodistribution.

The invention relates to octahydro-pyrrolo[3,4-b]pyrrole N-oxides as prodrugs of histamine-3 receptor ligands. As such, the prodrugs of the invention can be useful to treat disorders where modulation of histamine-3 receptor activity is of therapeutic benefit.

SUMMARY OF THE INVENTION

The invention is directed to octahydro-pyrrolo[3,4-b]pyrrole N-oxides having a compound of formula (I):

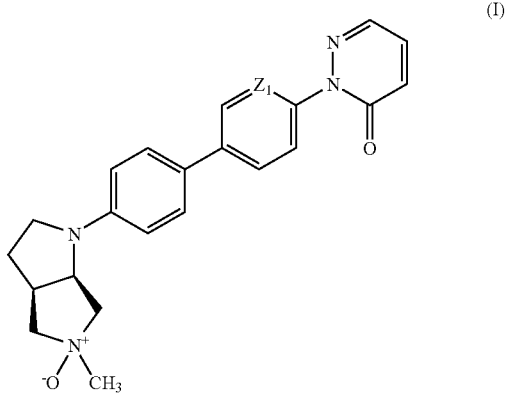

(I)

or a pharmaceutically acceptable salt, or polymorph thereof, wherein $Z_1$ is N or CH.

Another aspect of the invention relates to pharmaceutical compositions comprising compounds of the invention. Such compositions can be administered in accordance with a method of the invention, typically as part of a therapeutic regimen for treatment or prevention of conditions and disorders related to histamine-3 receptor activity.

Another aspect of the invention relates to a method of treating a mammal having a condition where modulation of histamine-3 receptor activity is of therapeutic benefit, said method comprising administering to a subject having or susceptible to said disorder with a therapeutically effective amount of a compound of the formula (I).

Another aspect of the invention is the use of a compound of formula (I)

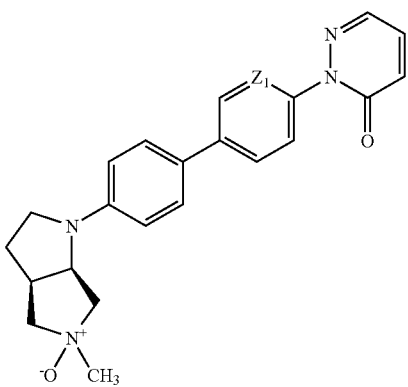

(I)

or a pharmaceutically acceptable salt, or polymorph thereof, as a prodrug of compounds of formula (II):

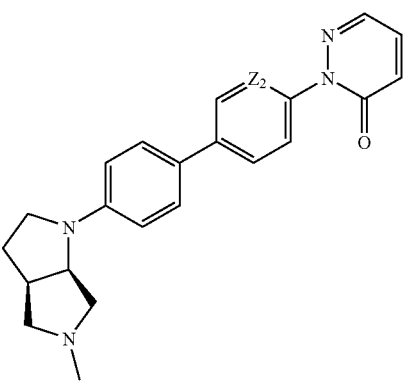

(II)

wherein $Z_2$ is N or CH, to treat a mammal having a condition or disorder where modulation of histamine-3 receptor activity is of therapeutic benefit, comprising administering to a subject having or susceptible to said condition or disorder a therapeutically effective amount of a compound of the formula (I).

Another aspect of the invention relates to a method for preparing compounds of formula (I).

Another aspect of the invention relates to a method of using a compound of formula (I) to selectively modulate histamine-3 receptor activity.

After oral administration or in vivo administration of compounds of formula (I), compounds of formula (II) are formed in animals. The compounds of formula (II) are potent histamine-3 receptor antagonists that are active and beneficial in animal models of central nervous system disease. The method is useful for treating, or preventing conditions and disorders related to histamine-3 receptor modulation in mammals. Such conditions and disorders include Alzheimer's disease, asthma, allergic rhinitis, attention-deficit hyperactivity disorder, deficits in attention, bipolar disorder, cognitive dysfunction, cognitive deficits in psychiatric disorders, deficits of memory, deficits of learning, dementia, cutaneous carcinoma, drug abuse, diabetes, type II diabetes, depression, epilepsy, gastrointestinal disorders, inflammation, insulin resistance syndrome, jet lag, medullary thyroid carcinoma, melanoma, Meniere's disease, vestibular disorders, metabolic syndrome, mild cognitive impairment, migraine, mood and attention alteration, motion sickness, narcolepsy, pathological sleepiness, neurogenic inflammation, obesity, obsessive compulsive disorder, pain, neuropathic pain, neuropathy, Parkinson's disease, polycystic ovary syndrome, schizophrenia, cognitive deficits of schizophrenia, seizures, septic shock, Syndrome X, Tourette's syndrome, vertigo, and sleep disorders. More particularly, the method is useful for treating or preventing conditions and disorders related to the central nervous system involving memory, cognitive and other neurological processes, obesity, and also peripheral and systemic activities, such those involved in asthma, allergic rhinitis and obesity. Accordingly, the compounds and compositions of the invention are useful as a medicament for treating or preventing histamine-3 receptor modulated disease.

The invention also relates to particular salts and polymorphs of certain compounds of the invention, as well as compositions comprising and processes for preparing such compounds, salts, and polymorphs. The invention also relates to compounds that are intermediates in processes for preparing the compounds, salts, and polymorphs described herein.

The compounds, compositions comprising the compounds, processes for making the compounds, methods for treating or preventing conditions and disorders by administering the compounds, radiolabelled forms of the compounds, particular salts of certain compounds, particularly polymorphs of certain compounds, and compositions containing such salts, polymorphs, and radiolabelled forms of the compounds are further described herein.

DETAILED DESCRIPTION OF THE INVENTION

Compounds of the Invention

Compounds of the invention can have the formula (I) as described in the Summary of the Invention:

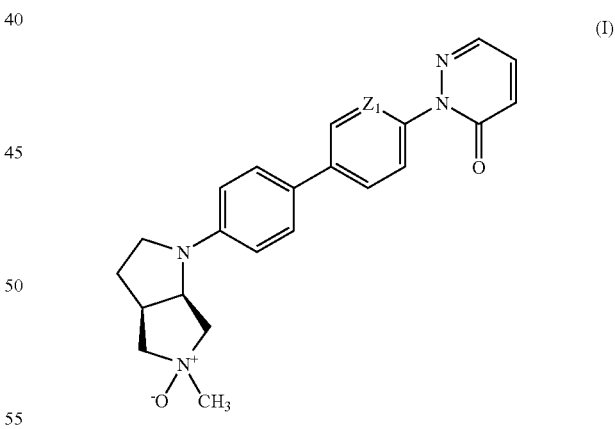

(I)

wherein $Z_1$ is N or CH.

There is also disclosed a pharmaceutical composition comprising a compound of formula (I) and a pharmaceutically acceptable carrier.

Preferred compounds of the invention are (3aR,5R,6aR)-5-methyl-1-(4'-(6-oxopyridazin-1(6H)-yl)biphenyl-4-yl)octahydropyrrolo[3,4-b]pyrrole 5-oxide, (3aR,5S,6aR)-5-methyl-1-(4'-(6-oxopyridazin-1(6H)-yl)biphenyl-4-yl) octahydropyrrolo[3,4-b]pyrrole 5-oxide, (3aR,5R,6aR)-5-methyl-1-(4-(6-(6-oxopyridazin-1(6H)-yl)pyridin-3-yl)phenyl)octahydropyrrolo[3,4-b]pyrrole 5-oxide, and (3aR,5S, 6aR)-5-methyl-1-(4-(6-(6-oxopyridazin-1(6H)-yl)pyridin-3-yl) phenyl)octahydropyrrolo[3,4-b]pyrrole 5-oxide.

More preferred are (3aR,5R,6aR)-5-methyl-1-(4'-(6-oxopyridazin-1(6H)-yl) biphenyl-4-yl)octahydropyrrolo[3,4-b]pyrrole 5-oxide, and (3aR,5S,6aR)-5-methyl-1-(4'-(6-oxopyridazin-1(6H)-yl)biphenyl-4-yl)octahydropyrrolo[3,4-b]pyrrole 5-oxide.

Most preferred is (3aR,5R,6aR)-5-methyl-1-(4'-(6-oxopyridazin-1(6H)-yl)biphenyl-4-yl) octahydropyrrolo[3,4-b]pyrrole 5-oxide.

Compounds of the invention were named by ACD/ChemSketch version 5.01 (developed by Advanced Chemistry Development Inc., Toronto, Ontario, Canada), or CHEMDRAW Ultra 9.0 software (CHEMDRAW is a registered trademark of CambridgeSoft Corporation of Cambridge, Mass.), or were given names consistent with ACD (Advanced Chemistry Development) nomenclature. The practice of assigning names to chemical compounds from structures and of assigning chemical structures from given chemical names is well-known to those of ordinary skill in the art.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC (International Union of Pure and Applied Chemistry) 1974 Recommendations, Section E: Fundamental Stereochemistry (*Pure & Appl. Chem.*, Vol. 45, pp. 11-30, (1976)). The invention contemplates various stereoisomers and mixtures thereof, and these are specifically included within the scope of this invention. Stereoisomers include enantiomers and diastereomers, and mixtures of enantiomers or diastereomers. Individual stereoisomers of compounds of the invention may be prepared synthetically from commercially available starting materials, which contain asymmetric or chiral centers, or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989); and Longman Scientific & Technical, Essex CM20 2JE, England, or (2) direct separation of the mixture of optical enantiomers on chiral chromatographic columns, or (3) fractional recrystallization methods.

Compounds of the invention may exist as cis or trans isomers, wherein substituents on a ring may be attached in such a manner that they are on the same side of the ring (cis) relative to each other, or on opposite sides of the ring relative to each other (trans). For example, cyclobutanes and cyclohexanes may be present in the cis or trans configuration and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art and may include separation of isomers by recrystallization or chromatography.

It should be understood that the compounds of the invention may possess tautomeric forms, as well as geometric isomers, and that these also constitute an aspect of the invention. It is also understood that the compounds of the invention may exist as isotopomers, wherein atoms may have different weights; for example, hydrogen, deuterium and tritium, or $^{12}C$, $^{11}C$ and $^{13}C$, or $^{19}F$ and $^{18}F$.

Methods of the Invention

Compounds and compositions of the invention of formula (I) are converted in vivo into compounds of formula (II), and therefore are useful as prodrugs of compounds of formula (II). Although compounds of formula (I) are not potent histamine-3 receptor antagonists or inverse agonists, compounds of formula (II) are potent histamine-3 receptor antagonists and inverse agonists. Therefore compounds of formula (I) are useful for modulating the effects of histamine-3 receptors. In particular, the compounds and compositions of the invention can be used for treating and preventing disorders modulated by histamine-3 receptors. Typically, such disorders can be ameliorated by modulating the histamine-3 receptors in a mammal, preferably by administering a compound or composition of the invention, either alone or in combination with another active agent, for example, as part of a therapeutic regimen. Such conditions or disorders can be selected from the group consisting of Alzheimer's disease, asthma, allergic rhinitis, attention-deficit hyperactivity disorder, deficits in attention, bipolar disorder, cognitive dysfunction, cognitive deficits in psychiatric disorders, deficits of memory, deficits of learning, dementia, cutaneous carcinoma, drug abuse, diabetes, type II diabetes, depression, epilepsy, gastrointestinal disorders, inflammation, insulin resistance syndrome, jet lag, medullary thyroid carcinoma, melanoma, Meniere's disease, vestibular disorders, metabolic syndrome, mild cognitive impairment, migraine, mood and attention alteration, motion sickness, narcolepsy, pathological sleepiness, neurogenic inflammation, obesity, obsessive compulsive disorder, pain, neuropathic pain, neuropathy, Parkinson's disease, polycystic ovary syndrome, schizophrenia, cognitive deficits of schizophrenia, seizures, septic shock, Syndrome X, Tourette's syndrome, vertigo, and sleep disorders.

In particular, a mammal having attention-deficit hyperactivity disorder, Alzheimer's disease, or dementia can benefit from the administration of a therapeutically effective amount of a compound of formula (I).

In particular, a mammal having schizophrenia or cognitive deficits of schizophrenia can benefit from the administration of a therapeutically effective amount of a compound of formula (I).

Additionally, a mammal having narcolepsy, sleep disorders, allergic rhinitis, asthma, or obesity can benefit from the administration of a therapeutically effective amount of a compound of formula (I).

As an important consequence of the ability of the compounds of the invention to generate compounds of formula (II) that modulate the effects of histamine-3 receptors in animals, the compounds and compositions of formula (I) are useful for treating and preventing diseases, conditions and disorders modulated by histamine-3 receptors. Accordingly, the compounds or compositions of the invention can be administered either alone or in combination with another active agent as part of a therapeutic regimen.

Compounds useful for the method of the invention, include but are not limited to, those specified in the Examples, and possess an affinity for the histamine-3 receptors. Preferred compounds of formula (I) useful for the methods disclosed herein are (3aR,5R,6aR)-5-methyl-1-(4'-(6-oxopyridazin-1(6H)-yl)biphenyl-4-yl) octahydropyrrolo[3,4-b]pyrrole 5-oxide, (3aR,5S,6aR)-5-methyl-1-(4'-(6-oxopyridazin-1(6H)-yl)biphenyl-4-yl)octahydropyrrolo[3,4-b]pyrrole 5-oxide, (3aR,5R,6aR)-5-methyl-1-(4-(6-(6-oxopyridazin-1

(6H)-yl)pyridin-3-yl) phenyl)octahydropyrrolo[3,4-b]pyrrole 5-oxide, and (3aR,5S,6aR)-5-methyl-1-(4-(6-(6-oxopyridazin-1(6H)-yl)pyridin-3-yl)phenyl)octahydropyrrolo[3,4-b]pyrrole 5-oxide. More preferred are (3aR,5R,6aR)-5-methyl-1-(4'-(6-oxopyridazin-1(6H)-yl)biphenyl-4-yl)octahydropyrrolo[3,4-b]pyrrole 5-oxide, and (3aR,5S,6aR)-5-methyl-1-(4'-(6-oxopyridazin-1(6H)-yl)biphenyl-4-yl)octahydropyrrolo[3,4-b]pyrrole 5-oxide. Most preferred is (3aR,5R,6aR)-5-methyl-1-(4'-(6-oxopyridazin-1(6H)-yl)biphenyl-4-yl) octahydropyrrolo[3,4-b]pyrrole 5-oxide.

Such compounds may be useful for the treatment and prevention of diseases, conditions, or disorders related to histamine-3 modulation. Examples of such diseases, conditions or disorders are, for example, Alzheimer's disease, asthma, allergic rhinitis, attention-deficit hyperactivity disorder, deficits in attention, bipolar disorder, cognitive dysfunction, cognitive deficits in psychiatric disorders, deficits of memory, deficits of learning, dementia, cutaneous carcinoma, drug abuse, diabetes, type II diabetes, depression, epilepsy, gastrointestinal disorders, inflammation, insulin resistance syndrome, jet lag, medullary thyroid carcinoma, melanoma, Meniere's disease, vestibular disorders, metabolic syndrome, mild cognitive impairment, migraine, mood and attention alteration, motion sickness, narcolepsy, pathological sleepiness, neurogenic inflammation, obesity, obsessive compulsive disorder, pain, neuropathic pain, neuropathy, Parkinson's disease, polycystic ovary syndrome, schizophrenia, cognitive deficits of schizophrenia, seizures, septic shock, Syndrome X, Tourette's syndrome, vertigo, and sleep disorders. The ability of histamine-3 receptor modulators and consequently, the compounds of the invention, to prevent or treat such diseases, conditions, or disorders is demonstrated by examples found in the following references.

The ability of the compounds of the invention, including but not limited to, those specified in the Examples, to treat attention-deficit hyperactivity disorder and deficits in attention, may be demonstrated by Cowart et al., *Journal of Medicinal Chemistry*, Vol. 48, pp. 38-55 (2005); Fox et al., "Pharmacological Properties of ABT-239: II. Neurophysiological Characterization and Broad Preclinical Efficacy in Cognition and Schizophrenia of a Potent and Selective Histamine H3 Receptor Antagonist", *Journal of Pharmacology and Experimental Therapeutics*, Vol. 313, pp. 176-190 (2005); Fox et al., "Effects of Histamine H3 Receptor Ligands GT-2331 and Ciproxifan in a Repeated Acquisition Avoidance Response in the Spontaneously Hypertensive Rat Pup", *Behavioural Brain Research*, Vol. 131(1,2), pp. 151-161 (2002); Yates et al., "Identification and Pharmacological Characterization of a Series of New 1H-4-Substituted-Imidazoyl Histamine H3 Receptor Ligands", *Journal of Pharmacology and Experimental Therapeutics*, Vol. 289, pp. 1151-1159 (1999); Ligneau et al., *Journal of Pharmacology and Experimental Therapeutics*, Vol. 287, pp. 658-666 (1998); Tozer, *Expert Opinion on Therapeutic Patents*, Vol. 10, p. 1045 (2000); Halpern, "GT-2331", *Current Opinion in Central and Peripheral Nervous System Investigational Drugs*, Vol. 1, pp. 524-527 (1999); Shaywitz et al., *Psychopharmacology*, Vol. 82, pp. 73-77 (1984); Dumery et al., "Development of Amygdaloid Cholinergic Mediation of Passive Avoidance Learning in the Rat," *Exp. Brain Res.*, Vol. 67 pp. 61-69 (1987); Tedford et al., "Pharmacological Characterization of GT-2016, A Non-Thiourea-Containing Histamine $H_3$ Receptor Antagonist: In Vitro and In Vivo Studies", *Journal of Pharmacology and Experimental Therapeutics*, Vol. 275, pp. 598-604 (1995); Tedford et al., "Abstracts", *Society for Neuroscience*, Vol. 22, p. 22 (1996); Glase et al., "Attention Deficit Hyperactivity Disorder: Pathophysiology and Design of New Treatments", *Annual Reports in Medicinal Chemistry*, Vol. 37, pp. 11-20 (2002); Schweitzer et al., "Drugs Under Investigation for Attention-Deficit Hyperactivity Disorder", *Current Opinion in Investigative Drugs*, Vol. 3, p. 1207 (2002).

The ability of the compounds of the invention, including but not limited to, those specified in the Examples, to treat dementia, and diseases with deficits of memory and learning, may be demonstrated by Fox et al., *Journal of Pharmacology and Experimental Therapeutics*, Vol. 305(3), pp. 897-908 (2003); Fox; *Inflammation Research*, Vol. 52 (Suppl. 1), pp. S31-S32 (2003); Bernaerts et al., *Behavioural Brain Research*, Vol. 154 pp. 211-219 (2004); Onodera et al., *Nauyn-Schmiedebergs' Arch. Pharmacol.*, Vol. 357, pp. 508-513 (1998); Prast et al., *Brain Research*, Vol. 734, pp. 316-318 (1996); Chen et al., *Brain Research*, Vol. 839, pp. 186-189 (1999); Passani et al., *Neuroscience and Biobehavioral Reviews*, Vol. 24, pp. 107-113 (2000).

The ability of the compounds of the invention, including but not limited to, those specified in the Examples, to treat schizophrenia, cognitive deficits of schizophrenia, and cognitive deficits, may be demonstrated by Fox et al., "Pharmacological Properties of ABT-239: II. Neurophysiological Characterization and Broad Preclinical Efficacy in Cognition and Schizophrenia of a Potent and Selective Histamine H3 Receptor Antagonist", *Journal of Pharmacology and Experimental Therapeutics*, Vol. 313, pp. 176-190 (2005); Browman et al., "Enhancement of Prepulse Inhibitor of Startle in Mice by the $H_3$ Receptor Antagonists Thioperamide and Ciproxifan", *Behavioural Brain Research*, Vol. 153(1), pp. 69-76 (2004); Komater et al., "$H_3$ Receptor Blockade by Thioperamide Enhances Cognition Without Inducing Locomotor Sensitization", *Psychopharmacology* (Berlin, Germany), Vol. 167(4), pp. 363-372 (2003); Rodrigues et al., *British Journal of Pharmacology*, Vol. 114(8), pp. 1523-1524 (1995); Passani et al., *Neuroscience and Biobehavioral Reviews*, Vol. 24, pp. 107-113 (2000); Morriset et al., *Journal of Pharmacology and Experimental Therapeutics*, Vol. 288, pp. 590-596 (1999).

The ability of the compounds of the invention, including but not limited to, those specified in the Examples, to treat dysfunction in psychiatric disorders, Alzheimer's disease, and mild cognitive impairment may be demonstrated by Meguro et al., *Pharmacology, Biochemistry and Behavior*, Vol. 50(3), pp. 321-325 (1995); Esbenshade et al., "Pharmacological and Behavioral Properties of A-349821, a Selective and Potent Human Histamine $H_3$ Receptor Antagonist", *Biochemical Pharmacology*, Vol. 68, pp. 933-945 (2004); Huang et al., *Behavioural Brain Research*, Vol. 151, pp. 287-293 (2004); Mazurkiewicz-Kwilecki et al., *Canadian Journal of Physiology and Pharmacology*, Vol. 67, pp. 75-78 (1989); Panula et al., *Neuroscience*, Vol. 82, pp. 993-997 (1997); Haas et al., *Behavioural Brain Research*, Vol. 66, pp. 41-44 (1995); De Almeida et al., *Arch. Int. Pharmacodyn.*, Vol. 283, pp. 193-198 (1986); Kamei et al., *Psychopharmacology*, Vol. 102, pp. 312-318 (1990); Kamei et al., *Japanese Journal of Pharmacology*, Vol. 57, pp. 437-482 (1991); Schwartz et al., *Psychopharmacology, The Fourth Generation of Progress*, Bloom and Kupfer (eds.), Raven Press, New York, p. 397 (1995); and Wada et al., *Trends in Neurosciences*, Vol. 14, p. 415 (1991).

The ability of the compounds of the invention, including but not limited to, those specified in the Examples, to treat epilepsy, and seizures, may be demonstrated by Harada et al., *Brain Research Bulletin*, Vol. 63, pp. 143-146 (2004); Yokoyama et al., *European Journal of Pharmacology*, Vol.

234, pp. 129-133 (1993); Yokoyama et al., *European Journal of Pharmacology*, Vol. 260, p. 23 (1994); Yokoyama et al., *CNS Drugs*, Vol. 5, p. 321 (1996); Vohora, *Life Sciences*, Vol. 66, pp. 297-301 (2000); Onodera et al., *Progress in Neurobiology*, Vol. 42, p. 685 (1994); Chen et al., *British Journal of Pharmacology*, Vol. 143, pp. 573-580 (2004); Leurs et al., *Progress in Drug Research*, Vol. 45, pp. 170-165 (1995); Leurs et al., *Progress in Drug Research*, Vol. 39, p. 127 (1992); Yokoyama et al., *CNS Drugs*, Vol. 5 (5) pp. 321-330 (1995); Hurukami et al., *Meth. Find. Exp. Clin. Pharmacol.*, Vol. 17 (C), pp. 70-73 (1995); and Yawata et al., *Molecular Brain Research*, Vol. 132, pp. 13-17 (2004).

The ability of the compounds of the invention, including but not limited to, those specified in the Examples, to treat allergic rhinitis and asthma, may be demonstrated by McLeod et al., *American Journal of Rhinology*, Vol. 13, pp. 391-399 (1999); McLeod et al., *Allergy*, Schering-Plough Research Institute, Kenilworth, N.J., USA.; Hansel et al., "New Drugs for Asthma, Allergy and COPD", *Progress in Respiratory Research*, Vol. 31, pp. 133-136 (2001); Delaunois et al., *European Journal of Pharmacology*, Vol. 277, pp. 243-250 (1995); Dimitriadou et al., *Clinical Science*, Vol. 87, pp. 151-163 (1994).

The ability of the compounds of the invention, including but not limited to, those specified in the Examples, to treat motion sickness, dizziness, Meniere's disease, vestibular disorders, and vertigo, may be demonstrated by Pan et al., *Methods and Findings in Clinical Pharmacology*, Vol. 20(9), pp. 771-777 (1998); O'Neill et al., *Methods and Findings in Clinical Pharmacology*, Vol. 21(4), pp. 285-289 (1999); Chavez et al., *Brain Research*, Vol. 1064, pp. 1-9 (2005); Leurs et al., *Progress in Drug Research*, Vol. 45, pp. 170-165 (1995); and Lozada et al., *BioMed Central Neuroscience*, Vol. 5, p. 32 (2004).

The ability of the compounds of the invention, including but not limited to, those specified in the Examples, to treat obesity, diabetes, type II diabetes, Syndrome X, insulin resistance syndrome, and metabolic syndrome, may be demonstrated by Hancock, *European Journal of Pharmacology*, Vol. 487, pp. 183-197 (2004); Hancock et al., *Inflamm. Res.*, Vol. 53, Supplement 1, S47-S48 (2004); Itoh et al., *Biological Psychiatry*, Vol. 45(4), pp. 475-481 (1999); Yates et al., *Abstracts, Society for Neuroscience,* 102.10:219 (November, 2000); Malmlof et al., *International Journal of Obesity*, Vol. 29, pp. 1402-1412 (2005); and Bjenning et al., *Abstracts, International Sendai Histamine Symposium*, Sendai, Japan, #P39 (November, 2000); Sakata et al., *Brain Research*, Vol. 537(1-2), pp. 303-306 (1990).

The ability of the compounds of the invention, including but not limited to, those specified in the Examples, to treat pain, including neuropathic pain and neuropathy, may be demonstrated by Malmberg-Aiello et al., *British Journal of Pharmacology*, Vol. 111(4), pp. 1269-1279 (1994); Hriscu, *Farmacia*, Vol. 49(2), pp. 23-30, (2001).

The ability of the compounds of the invention, including but not limited to, those specified in the Examples, to treat sleep disorders, including narcolepsy and pathological sleepiness, and jet lag, may be demonstrated by Barbier et al., *British Journal of Pharmacology*, pp. 1-13 (2004); Monti et al., *Neuropsychopharmacology*, Vol. 15, pp. 31-35 (1996); Lin et al., *Brain Research*, Vol. 523, pp. 325-330 (1990); Monti et al., *Neuropsychopharmacology*, Vol. 15, pp. 31-35 (1996); Ligneau et al., *Journal of Pharmacology and Experimental Therapeutics*, Vol. 287, pp. 658-666 (1998); Sakai et al., *Life Sciences*, Vol. 48, pp. 2397-2404 (1991); Mazurk-iewicz-Kwilecki et al., *Canadian Journal of Physiology and Pharmacology*, Vol. 67, pp. 75-78 (1989); Panula et al., *Neuroscience*, Vol. 44, pp. 465-481 (1998); Wada et al., *Trends in Neuroscience*, Vol. 14, p. 415 (1991); Monti et al., *European Journal of Pharmacology*, Vol. 205, p. 283 (1991); Dvorak et al., *Journal of Medicinal Chemistry*, Vol. 48, pp. 2229-2238 (2005).

The ability of the compounds of the invention, including but not limited to, those specified in the Examples, to treat drug abuse, may be demonstrated by Clapham et al., *European Journal of Pharmacology*, Vol. 259 (2), pp. 107-14 (1994). Amphetamine is an abused stimulant in humans. It, and similar abused drugs stimulate locomotor activity in animals, and it has been found that the histamine-3 antagonist thioperamide suppresses the locomotor stimulation induced by amphetamine. Therefore histamine-3 antagonists are likely to be useful for treating drug abuse as may be demonstrated by Clapham et al., *European Journal of Pharmacology*, Vol. 259 (2), pp. 107-14 (1994).

The ability of the compounds of the invention, including but not limited to, those specified in the Examples, to treat mood alteration, bipolar disorder, depression, obsessive compulsive disorder, and Tourette's syndrome, may be demonstrated by Lamberti et al., *British Journal of Pharmacology*, Vol. 123, pp. 1331-1336 (1998); Perez-Garcia et. al., *Psychopharmacology*, (Berlin) Vol. 142(2), pp. 215-20 (1999).

The ability of the compounds of the invention, including but not limited to, those specified in the Examples, to treat Parkinson's disease (a disease wherein patients have deficits in the ability to initiate movements, and patients' brains have low dopamine levels) may be demonstrated by Sánchez-Lemus et al., *Neuroscience Letters*, Vol. 364, pp. 179-184 (2004); Sakai et al., *Life Sciences*, Vol. 48, pp. 2397-2404 (1991); Fox et al., *Journal of Pharmacology and Experimental Therapeutics*, Vol. 313, pp. 176-190 (2005); Chen et al., *British Journal of Pharmacology*, Vol. 143, pp. 573-580 (2004).

The ability of the compounds of the invention, including but not limited to, those specified in the Examples, to treat medullary thyroid carcinoma, melanoma, polycystic ovary syndrome, may be demonstrated by *Polish Med. Sci. Mon.*, Vol. 4(5), p. 747 (1998); Szelag, *Medical Science Monitor*, Vol. 4(5), pp. 747-755 (1998); and Fitzsimons et al., *Inflammation Res.*, Vol. 47 (Suppl. 1), pp. S50-S51 (1998).

Compounds of the invention are particularly useful for treating and preventing a condition or disorder affecting attention-deficit hyperactivity, Alzheimer's disease, or dementia. Compounds of the invention are particularly useful for treating and preventing a condition or disorder affecting schizophrenia or cognitive deficits of schizophrenia. Compounds of the invention are particularly useful for treating and preventing a condition or disorder affecting narcolepsy, sleep disorders, allergic rhinitis, asthma, or obesity.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form, or where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dosage level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start dosages of the compound at levels lower than required to achieve the desired therapeutic effect and to gradually increase the dosage until the desired effect is achieved.

For treatment or prevention of disease, the total daily dosage of the compounds of this invention administered to a human or lower animal may range from about 0.0003 mg/kg to about 30 mg/kg of body weight. For purposes of oral administration, more preferable doses can be in the range of from about 0.001 mg/kg to about 0.1 mg/kg body weight. If desired, the effective daily dosage can be divided into multiple dosages for purposes of administration. Consequently, single dosage compositions may contain such amounts or submultiples thereof to make up the daily dosage.

Methods for Preparing Compounds of the Invention

The compounds of the invention can be better understood in connection with the following synthetic schemes and methods, which illustrate a means by which the compounds can be prepared.

Abbreviations which have been used in the descriptions of the schemes and the Examples that follow are: Xantphos for 4,5-bis(diphenylphosphino)-9,9-dimethylxanthene, [161265-03-8]; BINAP for 2,2'-bis(diphenylphosphino)-1, 1'-binaphthyl; Boc for butyloxycarbonyl; EtOAc for ethyl acetate; HPLC for high pressure liquid chromatography; IPA for isopropyl alcohol; Me for methyl; MeOH for methanol; Ms for methanesulfonyl; Pd for palladium; tBu for tert-butyl; TEA for triethylamine; TFA for trifluoroacetic acid; THF for tetrahydrofuran; and Ts for para-toluenesulfonyl; dba for dibenzylidine acetone; DCM for dichloromethane, $NH_4OH$ for saturated aqueous ammonium hydroxide; rt for room temperature or ambient temperature suitably ranging from 17-30° C. Copper iodide is CuI; palladium acetate is $Pd(OAc)_2$. Emrys process vial is a microwave process vial (10 ml or 30 ml glass vial with sealed cap) from PersonalChemistry AB (Uppsala). All microwave irradiation experiments were carried out using the Emrys synthesizer from PersonalChemistry AB (Uppsala). All experiments were carried out in sealed microwave process vials utilizing the standard absorbance level (300 W maximum power). If not stated otherwise, reaction times under microwave conditions reflect total irradiation times counted from the beginning of the irradiation. As identifiers of compounds available from descriptions reported in the literature or available commercially, CAS numbers may be used. CAS numbers are identifier numbers assigned to compounds by Chemical Abstracts Service of the American Chemical Society, and are well-known to those of ordinary skill in the art.

The compounds of this invention can be prepared by a variety of synthetic procedures. Specific procedures for the preparation of the compounds of formula (I) are given.

REFERENCE EXAMPLE A

The following Reference Examples describe synthesis of compounds used for preparation of compounds as described in the Examples. Such methods are intended only to provide examples of how such compounds can be obtained and are not intended to provide an exhaustive list of how to provide the desired compound.

REFERENCE EXAMPLE A

Ethyl (3aR,6aR)-hexahydropyrrolo[2,3-c]pyrrole-5 (1H)-carboxylate dibenzoyl-D-tartrate Salt Example A1

((R)-1-phenyl-ethylamino)-acetic Acid Methyl Ester

A reactor was charged with 10 g of R-methylbenzylamine, 100 mL of EtOAc, and 9.19 g of $Et_3N$. Methyl bromoacetate (15.15 g) was added and the mixture was heated to 50-60° C. for 10 hours with stirring. The mixture was then cooled to ambient temperature, then washed with 50 mL of water followed by 50 mL of 15% NaCl solution, to provide 100 g of an EtOAc solution which contained 15 g of (1-phenyl-ethylamino)-acetic acid methyl ester (96% yield).

Example A2

(1-(R)-phenyl-ethylamino)-acetic Acid

A solution of (1-(R)-phenyl-ethylamino)-acetic acid methyl ester (21.7 g of a solution in EtOAc) was concentrated, and the residue was taken up in 24 mL of water and heated at reflux for 13 hours. Upon completion, the mixture was concentrated under reduced pressure and 30 mL of isopropanol was added. The resulting precipitate was filtered and rinsed with 10 mL of isopropanol then dried under reduced pressure to provide 2.4 g of the title compound.

Example A3

Ethyl 1-((R)-1-phenylethyl)hexahydropyrrolo[2,3-c] pyrrole-5(1H)-carboxylate

A solution of (1-(R)-phenyl-ethylamino)-acetic acid (25.6 g) in 384 mL of toluene was heated to 90° C. To this 170 g (1.1 equivalents) of a 15.84 wt. % solution of allyl-(2-oxo-ethyl)-carbamic acid ethyl ester (U.S. Pat. No. 5,071,999) in toluene, was added over 20 minutes and the mixture was stirred at 90° C. for 14 hours then at 95° C. for 12 hours. After cooling, the product was extracted with 2×115 g of 20% citric acid solution. The citric acid solution was diluted with 205 mL of isopropyl acetate, and the mixture was neutralized with a solution of 51.2 g $K_2CO_3$ in 120 g water, and thoroughly shaken. The layers were separated, and the aqueous layer was extracted again with 102 mL of isopropyl acetate. The organic extracts were combined and distilled under reduced pressure to provide an oil which was then diluted with 125 mL of MeOH to provide 140 g (100% yield) of the title compound as a 30% by weight solution in MeOH.

Example A4

Ethyl hexahydropyrrolo[3,4-b]pyrrole-5(1H)-carboxylate

5% palladium hydroxide on activated carbon (13.9 g, 50% w/w in water) was added to a pressure reactor. The product of Example A3 (as 506.8 g of a 25.9 wt % solution of ethyl 1-((R)-1-phenylethyl)hexahydropyrrolo[2,3-c]pyrrole-5(1H)-carboxylate (131.3 g) in MeOH was added, followed by a MeOH rinse (37 g). The mixture was heated to 50° C. under an atmosphere of hydrogen (40 psi) for 4 hours. The mixture was filtered through HYFLO Filter Aid (HYFLO is a registered trademark of Celite Products Company of Los Angeles, Calif.) and rinsed with 200 mL of MeOH to provide a solution containing 78.9 g of the title compound.

Example A5

Ethyl (3aR,6aR)-hexahydropyrrolo[2,3-c]pyrrole-5(1H)-carboxylate dibenzoyl-D-tartrate Salt A solution of 150 g of ethyl hexahydropyrrolo[3,4-b]pyrrole-5(1H)-carboxylate (~11.2% wt in MeOH) was heated to 60° C. To this was added a solution of D-dibenzoyltartaric acid mono-hydrate (231.5 g) dissolved in MeOH (591 mL+95 mL rinse), and the mixture was stirred at 60±5° C. for 2 hours during which time crystallization occurred. The slurry was cooled to 18° C. over 6 hours, and the product was collected by filtration and rinsed with MeOH (2×330 mL). The product was dried at 40-45° C. to provide 198 g of the title compound. Chiral HPLC analysis of the Cbz-derivative ((3aR,6aR)-1-benzyl 5-ethyl hexahydropyrrolo[3,4-b]pyrrole-1,5-dicarboxylate. The Cbz group is an abbreviation for the carbobenzyloxy protecting group of the product and indicates that the product was obtained with 99% enantiomeric excess.

Example A6

(3aR,6aR)-5-Methyl-hexahydro-pyrrolo[3,4-b]pyrrole-1-carboxylic acid tert-butyl Ester To a solution of (3aR,6aR)-hexahydro-pyrrolo[3,4-b]pyrrole-1-carboxylic acid tert-butyl ester (18.31 g, 0.86 mol) in MeOH (450 ml) was added paraformaldehyde (52 g, 1.72 mole), and the mixture was stirred at room temperature for 1 hour. Sodium cyanoborohydride was then added, and the mixture was stirred at room temperature for 10 hours, diluted with 1N NaOH (450 ml), extracted with dichloromethane (5×200 ml). The combined organic layers were dried ($Na_2SO_4$), filtered and concentrated to provide the title compound. $^1$H NMR (300 MHz, DMSO-$d_6$) δ ppm 4.18 (m, 1 H) 3.47-3.59 (m, 1 H) 3.34-3.46 (m, 2 H) 2.75-2.90 (m, 1 H) 2.71 (m, 1 H) 2.44-2.60 (m, 2 H) 2.29 (s, 3 H) 1.89-2.06 (m, 1 H) 1.65-1.81 (m, 1 H) 1.42-1.49 (m, 9 H). MS: $(M+H)^+=226$.

(3aR,6aR)-hexahydro-pyrrolo[3,4-b]pyrrole-1-carboxylic acid tert-butyl ester (CAS #370880-09-4) may be prepared as described in Schenke et al, "Preparation of 2,7-Diazabicyclo[3.3.0]octanes", U.S. Pat. No. 5,071,999 (1991), which provides a racemate which may be resolved by chromatography on a chiral column or by fractional crystallization of diastereomeric salts, or as described in Basha et al., "Substituted Diazabicycloalkane Derivatives", U.S. Patent Publication Number 2005/0101602 (2005).

Example A7

(3aR,6aR)-5-Methyl-hexahydro-pyrrolo[3,4-b]pyrrole

To a solution of the product of Example A6 (20.8 g, 0.86 mole) in MeOH (450 ml) was added aqueous 3N HCl (300 ml). The mixture was stirred at room temperature overnight, then concentrated to dryness at 30° C. under vacuum. The residue was treated with aqueous 1N NaOH to obtain a pH of 9-10. The mixture was concentrated to dryness. The crude material was purified by chromatography (eluting with a mixture of 10% MeOH and 1% $NH_4OH$ in dichloromethane) to provide the title compound. $^1$H NMR (300 MHz, $CDCl_3$) δ ppm 4.12-4.17 (m, 1 H) 3.31-3.43 (m, 1 H) 3.19-3.30 (m, 1 H) 3.12 (d, J=11.53 Hz, 1 H) 2.88-3.01 (m, 1 H) 2.69 (dd, J=9.49, 2.37 Hz, 1 H) 2.40-2.52 (m, 2 H) 2.33 (s, 3 H) 2.12-2.28 (m, 1 H) 1.82-1.95 (m, 1 H). MS: $(M+H)^+=127$.

Example A8

(3aR,6aR)-1-(4-bromo-phenyl)-5-methyl-octahydro-pyrrolo[3,4-b]pyrrole

The product of Example A7 (2.30 g, 18.2 mmole), 1,4-dibromobenzene (5.16 g, 20.9 mmole), tris(dibenzylideneacetone)dipalladium (340 mg, 0.36 mmole), racemic-2,2'-bis(diphenylphosphino)-1,1'-binaphthyl (460 mg, 0.73 mmole) and sodium tert-butoxide (2.63 g, 27.3 mmole) were dissolved in 20 ml of toluene and heated to 70° C. under $N_2$ for 16 hours. The mixture was cooled to room temperature, diluted with water and extracted with dichloromethane (5×). The combined organics were dried over sodium sulfate, filtered and concentrated and purified by chromatography (eluting with a mixture of 5% MeOH in dichloromethane) to provide the title compound. $^1$H NMR (300 MHz, $CDCl_3$) δ ppm 7.25-7.30 (m, 2 H) 6.41-6.46 (m, 2 H) 4.07 (m, 1 H) 3.47 (ddd, J=9.1, 7.7, 5.9 Hz, 1 H) 3.19 (dt, J=8.9, 7.3 Hz, 1 H) 2.95 (m, 1 H) 2.68 (dd, J=9.0, 3.0 Hz, 1 H) 2.55-2.60 (m, 3 H) 2.32 (s, 3 H) 2.13-2.22 (m, 1 H) 1.88-1.98 (m, 1 H). MS: $(M+H)^+=281/283$.

Synthesis of Compounds of the Invention

EXAMPLES

The compounds and processes of the invention will be better understood by reference to the following Examples, which are intended as an illustration of and not a limitation upon the scope of the invention.

Unless otherwise described, reactions were carried out under ambient conditions (ranging from 17-27° C.), under nitrogen. Unless otherwise described, "column chromatography" means flash chromatography carried out using silica gel, a technique well-known to those of ordinary skill in the art of organic synthesis.

Example 1

(3aR,5R,6aR)-5-methyl-1-(4'-(6-oxopyridazin-1(6H)-yl)biphenyl-4-yl) octahydropyrrolo[3,4-b]pyrrole 5-oxide and (3aR,5S,6aR)-5-methyl-1-(4'-(6-oxopyridazin-1(6H)-yl)biphenyl-4-yl) octahydropyrrolo[3,4-b]pyrrole 5-oxide Example 1A (3aR,6aR)-1-(4'-bromo-biphenyl-4-yl)-5-methyl-octahydro-pyrrolo[3,4-b]pyrrole The title compound was prepared according to the procedure described in Example A8, substituting 4,4'-dibromobiphenyl for 1,4-dibromobenzene. ¹H NMR (300 MHz, CDCl₃) δ ppm 7.39-7.53 (m, 6 H) 6.60-6.66 (m, 2 H) 4.17-4.23 (m, 1 H) 3.52-3.61 (m, 1 H) 3.26-3.35 (m, 1 H) 2.98-3.05 (m, 1 H) 2.70-2.80 (m, 2 H) 2.58-2.64 (m, 2 H) 2.38 (s, 3 H) 2.15-2.26 (m, 1 H) 1.97 (m, 1 H). MS: (M+H)⁺=357/359.

Example 1B

2-{4'-[(3aR,6aR)-5-methylhexahydropyrrolo[3,4-b]pyrrol-1(2H)-yl]-1,1'-biphenyl-4-yl}pyridazin-3(2H)-one The product of Example 1A (4.54 g, 12.6 mmole), 3(2H)-pyridazinone (2.41 g, 25.2 mmole), copper powder (1.60 g, 25.2 mmole) and potassium carbonate (5.21 g, 37.7 mmole) were dissolved in 63 ml of quinoline and heated at 150° C. under N₂ for 48 hours. The mixture was cooled to room temperature, diluted with hexane (15 ml) and filtered through a CELITE filter (CELITE is a registered trademark of Johns-Manville Corporation of Denver, Colo.). The filtrate was concentrated under reduced pressure and the residue was purified by chromatography (eluting first with diethyl ether, followed by dichloromethane, then elution with a mixture of 5% MeOH in dichloromethane) to provide the title compound, 2-{4'-[(3aR,6aR)-5-methylhexahydropyrrolo [3,4-b]pyrrol-1(2H)-yl]-1,1'-biphenyl-4-yl}pyridazin-3(2H)-one. ¹H NMR (300 MHz, CDCl₃) δ ppm 7.91 (dd, J=3.73, 1.70 Hz, 1 H) 7.61-7.65 (m, 4 H) 7.51 (d, J=8.48 Hz, 2 H) 7.25 (dd, dd, J=9.40, 4.07 Hz, 1 H) 7.07 (dd, J=9.49, 1.70 Hz, 1 H) 6.64 (d, J=8.81 Hz, 2 H) 4.19-4.27 (m, 1 H) 3.54-3.64 (m, 1 H) 3.28-3.38 (m, 1 H) 3.00-3.11 (m, 1 H) 2.56-2.85 (m, 4 H) 2.40 (s, 3 H) 2.10-2.29 (m, 1 H) 1.89-2.05 (m, J=6.78 Hz, 1 H); MS (M+H)⁺=373. The solid (3aR,6aR)-2-[4'-(5-methyl-hexahydro-pyrrolo [3,4-b]pyrrol-1-yl)-biphenyl-4-yl]-2H-pyridazin-3-one obtained showed a melting range of 204-207° C. (dec.).

Alternatively, (3aR,6aR)-2-[4'-(5-methyl-hexahydro-pyrrolo[3,4-b]pyrrol-1-yl)-biphenyl-4-yl ]-2H-pyridazin-3-one, the product of Example 1B, can be prepared according to the following procedure:

Example 1C

Ethyl (3aR,6aR)-hexahydropyrrolo[3,4-b]pyrrole-5(1H)-carboxylate

The product of Example A5 (205 g) and CH₂Cl₂ (1 L) were combined and cooled to 0° C. 1.54 L of a 20% KOH solution was cooled to 0° C. then slowly added to the salt slurry, and the biphasic reaction mixture was stirred vigorously at 0° C. After 2.75 hours, the layers were separated and the aqueous layer was extracted with CH₂Cl₂ (1 L). The organic layers were combined and concentrated under reduced pressure, then chased with toluene (1.6 L) to provide 386 g of a 19 wt % solution of product (100%).

Example 1D

Ethyl (3aR,6aR)-1-(4'-bromo-1,1'-biphenyl-4-yl)hexahydropyrrolo[3,4-b]pyrrole-5(1H)-carboxylate To a vessel containing 4,4'-dibromobiphenyl (12.48 g, 2.0 equiv.) and cesium carbonate (13.04 g, 2.0 eq.) was added the product of Example 1C (17.9 wt %, 20.6 g, 1.0 eq.) after which the vessel was evacuated and purged. A catalyst solution was prepared in a separate vessel by mixing Xantphos (0.77 g, 0.067 eq.) and palladium (II) acetate (0.22 g, 0.049 eq.) and degassed after which 17.3 g of toluene was added with stirring.

The catalyst solution was added to the vessel containing the 4,4'-dibromobiphenyl, cesium carbonate, and the product of Example 41C and the mixture was heated to 98° C. for 12 hours. The mixture was cooled to 20° C. and 80 g of dichloromethane was added. The resulting mixture was stirred and then filtered to remove the catalyst. The resulting solution was concentrated under reduced pressure and the residue was purified by column chromatography to yield 5.65 g of the title compound.

Example 1E

Ethyl (3aR,6aR)-1-[4'-(6-oxopyridazin-1(6H)-yl)-1,1'-biphenyl-4-yl]hexahydropyrrolo[3,4-b]pyrrole-5(1H)-carboxylate A mixture of 1.98 g of copper (I) iodide (10.4 mmole, 0.10 eq.), 1.66 g of 8-hydroxyquinoline (11.44 mmole, 0.11 eq.), 4.0 g of potassium carbonate (28.94 mmole, 0.29 eq.) in 18.8 g of dimethylformamide (DMF) was mixed at ambient temperature. The mixture was added to another flask containing 41.6 g of the product of Example 1D (100.16 mmole, 1.00 eq.), 23.6 g of potassium carbonate (170.75 mmole, 1.70 eq.), and 14.4 g of 3(2H)-pyridazinone (149.86 mmole, 1.50 eq.). Additional DMF (226 g) was used to transfer the catalyst slurry. The resulting mixture was deoxygenated then heated to 140° C. for about 18 hours. After cooling to ambient temperature, the mixture was diluted with 567 g of THF and 384 g of 10% NaCl solution. The mixture was filtered to remove excess salts and the aqueous phase was separated and back extracted with an additional 177 g of THF. The combined organic phases were then washed with 10% NaCl solution (3×384 g). The organic phase was concentrated under reduced pressure and MeOH (253 g) was added and the contents were concentrated under reduced pressure. After adding additional MeOH (158 g), the contents were cooled to 0° C., filtered, and washed with cold MeOH. The resulting solids were transferred to a vacuum oven to yield 35.31 g (81.9% yield). Mass Spectroscopy: 431.5 (m.w. 430.5). ¹H NMR (400 MHz, DMSO-d6) δ ppm 1.15 (s, 3 H), 1.78-1.88 (m, 1 H), 2.10 (ddd, J=12.49, 6.17, 6.04 Hz, 1H), 3.03 (s, 1 H), 3.24-3.35 (m, 5 H), 3.53 (ddd, J=9.23, 6.86, 6.69 Hz, 2 H), 3.67 (s, 1 H), 4.00 (s, 2 H), 4.22 (s, 1 H), 6.63 (d, J=8.51 Hz, 2 H), 7.07 (dd, J=9.47, 1.51 Hz, 1 H), 7.48 (dd, J=9.47, 3.84 Hz, 1 H), 7.53-7.60 (m, 4 H), 7.68 (d, J=8.64 Hz, 2 H), 8.06 (dd, J=3.84, 1.51 Hz, 1 H). ¹³C NMR (100 MHz, DMSO-d6) δ ppm 14.79 (CH3), 28.89 (CH₂), 47.71 (CH₂), 60.24 (CH₂), 112.34 (CH), 124.87 (CH), 125.27 (CH), 126.02 (C), 126.89 (CH), 130.05 (CH), 131.69 (CH), 136.87 (CH), 138.78 (C), 139.31 (C), 145.61 (C), 153.53 (C), 158.64 (C).

Example 1F

2-[4'-[(3aR,6aR)-hexahydropyrrolo[3,4-b]pyrrol-1(2H)-yl]-1,1'-biphenyl-4-yl]pyridazin-3(2H)-one A mixture of the product of Example 1E (7.50 g, 17.42 mmol) in 33% HBr in acetic acid (37 mL, 205.57 mmol, 11.8 equivalents) was heated to 65-70° C. for at least 6 hours while monitored by HPLC analysis for completion. When reaction is complete, the mixture is cooled to not more than 45° C. and is diluted with MeOH (111 mL). The mixture was cooled to 20-25° C., the product is collected by filtration and is washed with fresh MeOH (50 mL). The wet cake is dried in the vacuum oven at not more than 55° C. to provide the title compound (7.25 g, 94.8%).

Example 1G

2-[4'-(3aR,6aR)-(5-methylhexahydropyrrolo[3,4-b] pyrrol-1(2H)-yl)-1,1'-biphenyl-4-yl ]pyridazin-3 (2H)-one To a stirred solution of the product of Example 1F (13.80 g, 31.41 mmol) in dimethylacetamide (500 mL) was added a solution of 37% aqueous formaldehyde (7.2 mL, 94.23 mmol, 3.0 equivalents) followed by sodium triacetoxyborohydride (20.0 g, 94.23 mmol, 3.0 equivalents). The mixture was stirred at 25+/−5° C. for 30 minutes during which the starting material was consumed, giving a clear solution. The mixture was diluted with 1N HCl (94 mL, 94 mmol, 3 equivalents) and stirred for one hour. The mixture was adjusted to pH 9.0+/− 0.5 with 1N NaOH (335 mL). The mixture was stirred for 1 hour then filtered. The wet cake was washed with water and dried in a vacuum oven at about 50° C. to provide the title compound, 2-[4'-(3aR,6aR)-(5-methylhexahydropyrrolo[3, 4-b]pyrrol-1(2H)-yl)-1,1'-biphenyl-4-yl ]pyridazin-3(2H)- one (10.40 g, 88.9%).

Example 1H (3aR,5R,6aR)-5-methyl-1-(4'-(6-oxopyridazin-1 (6H)-yl)biphenyl-4-yl) octahydropyrrolo[3,4-b]pyr- role 5-oxide A solution of the product from Example 1G (5 g, 13.44 mmol) in DCM (80 mL) and MeOH (40 mL) was treated with hydrogen peroxide (5.2 mL, 30% in $H_2O$, 53.8 mmol). The mixture was heated to 50° C. for 48 hours. The mixture was concentrated under reduced pressure to a smaller volume while still in a solution. The solution was loaded onto an ANALOGIX SuperFlash silica gel column (ANALOGIX is a registered trademark of Analogix Inc. of Burlington, Wis.) and eluted with $NH_4OH$/MeOH/DCM (1/10/90) to obtain the faster moving component (comparing with Example 1I) as the title product. $^1$H NMR (300 MHz, DMSO) δ ppm 8.06 (m, 1H), 7.69 (d, J=9 Hz, 2 H), 7.57 (d, J=9 Hz, 4 H), 7.50 (d, J=6 Hz, 1 H), 7.08 (dd, dd, J=9, 4.0 Hz, 1 H), 6.70 (d, J=9 Hz, 2 H), 4.72 (d, J=6 Hz, 1 H), 3.75-3.82 (m, 1 H), 3.52-3.59 (m, 2 H), 3.36-3.45 (m, 3 H), 3.15-3.21 (m, 1 H), 3.14 (s, 3 H), 2.05- 2.12 (m, 1 H), 1.80-1.86 (m, 1 H); MS (DCI,) M$^+$=388.

Example 1I (3aR,5S,6aR)-5-methyl-1-(4'-(6-oxopyridazin-1 (6H)-yl)biphenyl-4-yl)octahydropyrrolo[3,4-b]pyr- role 5-oxide A solution of the product from Example 1G (5 g, 13.44 mmol) in DCM (80 mL) and MeOH (40 mL) was treated with hydrogen peroxide (5.2 mL, 30% in H2O, 53.8 mmol). The mixture was heated to 50° C. for 48 hours. The mixture was concentrated under reduced pressure to a smaller volume while still in a solution. The solution was loaded onto an ANALOGIX SuperFlash silica gel column (ANALOGIX is a registered trademark of Analogix Inc. of Burlington, Wis.) and eluted with $NH_4OH$/MeOH/DCM (1/10/90) to obtain the slower moving component (comparing with Example 1H) as the title product. $^1$H NMR (300 MHz, DMSO) δ ppm 8.07 (m, 1 H), 7.70 (d, J=9 Hz, 2 H), 7.57 (d, J=9 Hz, 4 H), 7.50 (d, J=6 Hz, 1 H), 7.08 (dd, dd, J=9, 4.0 Hz, 1 H), 6.65 (d, J=9 Hz, 2 H), 4.48-4.54 (m, 1 H), 3.81-3.87 (m, 1 H), 3.66-3.74 (m, 2 H), 3.36-3.42 (m, 2 H), 3.24 (m, 1 H), 3.09 (s, 3 H), 2.11-2.17 (m, 1 H); MS (DCI,) M$^+$=388.

Example 2

2-(5-{4-[(3aR,6aR)-5-methylhexahydropyrrolo[3,4- b]pyrrol-1(2H)-yl]phenyl}pyridin-2-yl) pyridazin-3 (2H)-one

Example 2A

Tert-butyl (3aR,6aR)-1-(4-bromophenyl)hexahydro- pyrrolo[3,4-b]pyrrole-5(1H)-carboxylate A mixture of tert-butyl (3aR,6aR)-hexahydropyrrolo[3,4- b]pyrrole-5(1H)-carboxylate (1, 1.5 g, 7.0 mmol), 1,4-dibro- mobenzene (2.8 g, 20.4 mmol), $Pd_2(dba)_3$ (275 mg, 0.3 mmol), BINAP (375 mg, 0.6 mmol) and sodium tert-butoxide (1.93 g, 20.0 mmol) were placed in glass microwave tubes and then purged three times with $N_2$ gas, followed by the addition of toluene (45 mL). The mixture was heated to 140° C. for 15 minutes in a microwave reactor. The mixture was then cooled to room temperature, was filtered, and the crude mixture was purified via chromatography ($SiO_2$, O-25% EtOAc:hexanes) to provide the title compound. $^1$H NMR (300 MHz, CDCl$_3$): δ=7.30 ppm (m, 2H), 7.39 (m, 2H), 4.11 (m, 1H), 3.57 (m, 3H), 3.31 (m, 3H), 2.99 (m, 1H), 2.15 (m, 1H), 1.92 (m, 1H), 1.43 (s, 9H). MS (ESI, M+1): 310.9.

Tert-butyl (3aR,6aR)-hexahydropyrrolo[3,4-b]pyrrole-5 (1H)-carboxylate (CAS #370882-39-6) may be prepared by the method described in Schrimpf et al., "Diazabicyclic Cen- tral Nervous System Active Agents", WO 2001/081347(A2) (2001).

Example 2B (3aR,6aR)-1-(4-bromophenyl)-5-methyloctahydro- pyrrolo[3,4-b]pyrrole To a solution of (3aR,6aR)-tert-butyl 1-(4-bromophenyl) hexahydropyrrolo[3,4-b]pyrrole-5(1H)-carboxylate (1.86 g, 5.1 mmol) in $CH_2Cl_2$ (50 mL) at 23° C. was added TFA (8 mL) and the mixture was allowed to stir for 2 hrs. The solvents were removed under vacuum and the residue was taken up in MeOH (50 mL) followed by the addition of formaldehyde (37%, 3 mL, 40 mmol) and $NaBH_3CN$ (950 mg, 15.1 mmol). The mixture was stirred at 23° C. for 10 hours, concentrated under reduced pressure and the residue was dissolved in $CH_2Cl_2$ (100 mL), washed sequentially with water (2×50 mL), brine (1×30 mL), and dried over $Na_2SO_4$, filtered and concentrated under reduced pressure. The crude product mix- ture was purified via chromatography ($SiO_2$, O-10% MeOH in $CH_2Cl_2$) to provide the title compound. $^1$H NMR (300 MHz, CDCl$_3$): δ=7.28 ppm (m, 2H), 6.44 (m, 2H), 4.05 (m, 1H), 3.45 (m, 1H), 3.19 (m, 1H), 2.94 (m, 1H), 2.67 (m, 1H), 2.52 (m, 3H), 2.30 (s, 3H), 2.16 (m, 1H), 1.95 (m, 1H). MS (ESI, M+1): 280.8.

Example 2C (3aR,6aR)-5-methyl-1-(4-(4,4,5,5-tetramethyl-1,3- dioxaborolan-2-yl)phenyl)octa-hydropyrrolo[3,4-b] pyrrole (3aR,6aR)-1-(4-bromophenyl)-5-methyloctahydropyrrolo [3,4-b]pyrrole (1.0 g, 3.6 mmol), bis(pinacolato)diboron (4,4, 4',4',5,5,5',5'-octamethyl-2,2'-bi(1,3,2-dioxaborolane, (1.0 g, 3.9 mmol), Pd(dppf)Cl$_2$CH$_2$Cl$_2$ (100 mg, 0.12 mmol) and KOAc (1150 mg, 11.7 mmol) were placed in a sealed microwave reaction tube, and purged three times with N$_2$ gas. Dioxane (20 mL) was added, and the mixture was heated at 150° C. for 15 minutes. After cooling down to 23° C., the mixture was filtered, and solvent was removed under reduced pressure. The mixture was then purified via chromatography (SiO$_2$, 10-60% EtOAc in hexanes) to provide the title compound. $^1$H NMR (300 MHz, CDCl$_3$): δ=7.67 ppm (m, 2H), 6.54 (m, 2H), 4.21 (m, 1H), 3.52 (m, 1H), 3.33 (m, 1H), 2.97 (m, 1H), 2.67 (m, 2H), 2.57 (m, 2H), 2.34 (br, 3H), 2.15 (m, 1H), 1.95 (m, 1H), 1.32 (s, 12H). MS (ESI, M+1): 329.1.

Example 2D 2-(5-bromopyridin-2-yl)pyridazin-3(2H)-one and 2-(6-bromopyridin-3-yl)pyridazin-3(2H)-one 3-pyridazinone (300 mg, 3.1 mmol), 2,5-dibromopyridine (1.0 g, 4.2 mmol), copper powder (200 mg, 3.1 mmol) and K$_2$CO$_3$ (1.29 g, 9.3 mmol) were placed in a sealed microwave tube, and purged three times with N$_2$ gas, followed by the addition of pyridine (15 mL). The mixture was heated to 120° C. in a microwave reactor for 40 minutes. The mixture was concentrated under reduced pressure after which the residue was taken up in CH$_2$Cl$_2$/MeOH, filtered and concentrated under reduced pressure. The crude mixture was purified via chromatography (SiO2, 10-80% EtOAc in hexanes) to provide the title compounds.

2-(5-bromopyridin-2-yl)pyridazin-3(2H)-one. $^1$H NMR (300 Mhz, CDCl$_3$): δ=8.72 ppm (s(br), 1H), 7.99 (m, 2H), 7.68 (d(br), J=8.4 Hz, 1H), 7.29 (dd (br), J=8.4, 3.7 Hz, 1H), 7.07 (dd, J=9.5, 1.7 Hz, 1H). MS (ESI, M+1): 253.8.

2-(6-bromopyridin-3-yl)pyridazin-3(2H)-one. $^1$H NMR (300 MHz, CDCl$_3$): δ=8.76 ppm (d, J=3.4 Hz, 1H), 7.98 (dd, J=8.5, 2.7 Hz, 1H), 7.94 (dd, J=2.7, 1.7 Hz, 1H), 7.59 (d, J=8.4 Hz, 1H), 7.29 (dd, J=8.4, 3.4 Hz, 1H), 7.06 (dd, J=8.5, 1.7 Hz, 1H). MS (ESI, M+1): 253.8.

Example 2E 2-(5-(4-((3aR,6aS)-5-methylhexahydropyrrolo[3,4-b]pyrrol-1(2H)-yl)phenyl)pyridin-2-yl) pyridazin-3(2H)-one (3aR,6aR)-5-methyl-1-(4-(4,4,5,5-tetramethyl-1,3-dioxaborolan-2-yl) phenyl)octa-hydro-pyrrolo[3,4-b]pyrrole (50 mg, 0.15 mmol), 2-(5-bromopyridin-2-yl) pyridazin-3(2H)-one (42 mg, 0.17 mmol), Pd(PPh$_3$)$_2$Cl$_2$ (11 mg, 0.01 mmol), 2-(dicyclohexylphosphino) biphenyl (5.6 mg, 0.016 mmol) and Na$_2$CO$_3$ (1M, 225 μL) were placed in a microwave tube, purged with N$_2$ and a mixture of solvents (EtOH:dioxane=1:1, 1 mL) was added. The mixture was heated to 140° C. in a microwave reactor for 15 minutes, cooled to ambient temperature, was filtered, and concentrated under reduced pressure. The residue was purified via chromatography (SiO$_2$, 0-10% MeOH in CH$_2$Cl$_2$) to provide the title compound, 2-(5-(4-((3aR,6aS)-5-methylhexahydropyrrolo [3,4-b]pyrrol-1(2H)-yl)phenyl)pyridin-2-yl)pyridazin-3(2H)-one. $^1$H NMR (300 MHz, CDCl$_3$): δ=8.82 ppm (d, J=2.8 Hz, 1H), 7.98 (m, 2H), 7.73 (d, J=8.2 Hz, 1H), 7.52 (m, 2H), 7.28 (dd, J=10.1, 3.7 Hz, 1H), 7.09 (dd, J=10.1, 1.7 Hz, 1H), 6.67 (m, 2H), 4.39 (m, 1H), 3.66 (m, 1H), 3.30 (m, 3H), 2.87 (m, 2H), 2.59 (s(br), 3H), 2.23 (m, 2H), 2.05 (m, 1H). MS (ESI, M+1): 374.2.

Example 2F (3aR,5R,6aR)-5-methyl-1-(4-(6-(6-oxopyridazin-1(6H)-yl)pyridin-3-yl) phenyl)octahydropyrrolo[3,4-b]pyrrole 5-oxide A solution of the product from Example 2E (23 mg, 0.062 mmol) in DCM (0.5 mL) and MeOH (1 mL) was treated with hydrogen peroxide (0.04 mL, 30% in H$_2$O, 0.24 mmol). The mixture was screw-capped in a 4 mL vial and heated to 50° C. for 24 hours. The mixture was concentrated under reduced pressure to a smaller volume while still in a solution. The solution was loaded onto an ANALOGIX SuperFlash silica gel column (ANALOGIX is a registered trademark of Analogix Inc. of Burlington, Wis.) and eluted with NH4OH/MeOH/DCM (1/10/90) to obtain the faster moving component (comparing with Example 2G) as the title product, (3aR,5R,6aR)-5-methyl-1-(4-(6-(6-oxopyridazin-1(6H)-yl) pyridin-3-yl) phenyl)octahydropyrrolo[3,4-b]pyrrole 5-oxide. $^1$H NMR (500 MHz, METHANOL-D4) δ ppm 1.25-1.31 (m, 1 H) 1.94-2.00 (m, J=19.22 Hz, 1 H) 2.21-2.29 (m, J=37.84 Hz, 1 H) 3.26-3.28 (m, 3 H) 3.47 (d, J=27.77 Hz, 1 H) 3.55 (d, J=25.33 Hz, 1 H) 3.66 (none, 1 H) 4.03 (dd, J=11.44, 8.09 Hz, 1 H) 6.78 (d, J=8.54 Hz, 1 H) 7.12 (dd, J=9.76, 1.53 Hz, 1 H) 7.53 (dd, J=9.61, 3.81 Hz, 1 H) 7.62 (d, J=8.85 Hz, 2 H) 7.65 (d, J=8.54 Hz, 1 H) 8.19 (dd, J=8.24, 2.44 Hz, 1 H) 8.76 (d, J=2.14 Hz, 1 H). MS (DCI,) M$^+$=389.

Example 2G (3aR,5S,6aR)-5-methyl-1-(4-(6-(6-oxopyridazin-1(6H)-yl)pyridin-3-yl) phenyl)octahydropyrrolo[3,4-b]pyrrole 5-oxide A solution of the product from Example 2E (23 mg, 0.062 mmol) in DCM (0.5 mL) and MeOH (1 mL) was treated with hydrogen peroxide (0.04 mL, 30% in H2O, 0.24 mmol). The mixture was screw-capped in a 4 mL vial and heated to 50° C. for 24 hours. The mixture was concentrated under reduced pressure to a smaller volume while still in a solution. The solution was loaded onto an ANALOGIX SuperFlash silica gel column (ANALOGIX is a registered trademark of Analogix Inc. of Burlington, Wis.) and eluted with NH4OH/MeOH/DCM (1/10/90) to obtain the slower moving component (comparing with Example 2F) as the title product, (3aR,5S,6aR)-5-methyl-1-(4-(6-(6-oxopyridazin-1(6H)-yl) pyridin-3-yl) phenyl)octahydropyrrolo[3,4-b]pyrrole 5-oxide. (3aR,5S,6aR)-5-methyl-1-(4-(6-(6-oxopyridazin-1(6H)-yl)pyridin-3-yl)phenyl)octahydropyrrolo[3,4-b]pyrrole 5-oxide. 1H NMR (501 MHz, METHANOL-D4) δ ppm 1.27-1.30 (m, 1 H) 2.25-2.30 (m, 1 H) 3.25 (s, 3 H) 3.35-3.48 (m, 3 H) 3.52-3.57 (m, J=21.09 Hz, 1 H) 3.71 (q, 1 H) 3.82 (dd, J=11.41, 8.34 Hz, 1 H) 4.02 (dd, J=12.08, 6.52 Hz, 1 H) 4.62-4.67 (m, J=19.36 Hz, 1 H) 6.73 (d, J=8.82 Hz, 1 H) 7.09 (dd, J=9.39, 1.53 Hz, 1 H) 7.49 (dd, J=9.39, 3.83 Hz, 1 H) 7.59 (d, J=8.82 Hz, 1 H) 7.61 (d, J=8.43 Hz, 1 H) 8.03 (dd, J=3.83, 1.53 Hz, 1 H) 8.15 (dd, J=8.24, 2.49 Hz, 1 H) 8.72 (d, J=2.11 Hz, 1 H). MS (DCI) M$^+$=389.

Pharmaceutical Compositions of the Invention

The invention also provides pharmaceutical compositions comprising a therapeutically effective amount of a compound of formula (I), or suitable salts and polymorphs thereof, in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection, or for rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants that can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally", as used herein, refers to modes of administration, which include intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils such as olive oil, and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof. If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions, which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is/are mixed with at least one inert pharmaceutically acceptable carrier, such as sodium citrate or dicalcium phosphate, and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons. Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., *Methods in Cell Biology*, Volume XIV, Academic Press, New York, N.Y., (1976), p. 33, et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Opthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts, esters, or amides derived from inorganic or organic acids. The phrase "pharmaceutically acceptable salts, esters and amides", as used herein, refers to carboxylate salts, amino acid addition salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid or inorganic acid.

Representative acid addition salts include, but are not limited to, ascorbic acid, (D)-tartaric acid, (L)-tartaric acid, phosphoric acid, salicylic acid, sulfuric acid, trifluoroacetic acid, and hydrochloric acid.

The basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine, and the like. Other representative organic amines useful for the formation of base addition salts include ethylenediamine, ethanolamine, diethanolamine, piperidine, and piperazine.

Determination of Biological Activity

To determine the effectiveness of representative compounds of this invention as histamine-3 receptor ligands, the following tests were conducted according to previously described methods (see Arrang et al, "Histamine $H_3$ Receptor Binding Sites in Rat Brain Membranes:Modulations by Guanine Nucleotides and Divalent Cations", *European Journal of Pharmacology*, Vol. 188, pp. 219-227 (1990); Tedford et al., "Pharmacological Characterization of GT-2016, A Non-Thiourea-Containing Histamine $H_3$ Receptor Antagonist: In Vitro and In Vivo Studies", *The Journal of Pharmacology and Experimental Therapeutics*, Vol. 275, pp. 598-604 (1995);

Leurs et al., "Histamine Homologues Discriminating Between Two Functional $H_3$-Receptor Assays. Evidence for $H_3$ Receptor", *Journal of Pharmacology and Experimental Therapeutics*, Vol. 276, No. 3, pp. 1009-1015 (1996); and Cheng et al., "Relationship Between the Inhibition Constant (K1) and the Concentration of Inhibitor which Causes 50% Inhibition (150) of an Enzymatic Reaction", *Biochemical Pharmacology*, Vol. 22., pp. 3099-3108 (1973)).

In vitro Binding Assays

The rat histamine-3 receptor was cloned and expressed in cells, and competition binding assays carried out, according to methods previously described (see Esbenshade et al., "Pharmacological Properties of ABT-239 [4-(2-{2-[(2R)-2-Methylpyrrolidinyl ]ethyl}-benzofuran-5-yl)benzonitrile]: I. Potent and Selective Histamine H3 Receptor Antagonist with Drug-Like Properties", *Journal of Pharmacology and Experimental Therapeutics*, Vol. 313, pp. 165-175, (2005); Esbenshade et al., "Pharmacological and Behavioral Properties of A-349821, a Selective and Potent Human Histamine $H_3$ Receptor Antagonist", *Biochemical Pharmacology*, Vol 68, pp. 933-945 (2004); Krueger et al., "G Protein-Dependent Pharmacology of Histamine $H_3$ Receptor Ligands: Evidence for Heterogeneous Active State Receptor Conformations", *Journal of Pharmacology and Experimental Therapeutics*, Vol. 314, pp. 271-281 (2005)). Membranes were prepared from C6 or HEK293 cells, expressing the rat histamine-3 receptor, by homogenization on ice in TE buffer (50 mM Tris-HCl buffer, pH 7.4, containing 5 mM EDTA), 1 mM benzamidine, 2 µg/ml aprotinin, 1 µg/ml leupeptin, and 1 µg/ml pepstatin. The homogenate was centrifuged at 40,000 g for 20 minutes at 4° C. This step was repeated, and the resulting pellet was resuspended in TE buffer. Aliquots were frozen at −70° C. until needed. On the day of assay, membranes were thawed and diluted with TE buffer.

Membrane preparations were incubated with $[H_3]$-N-α-methylhistamine (0.5-1.0 nM) in the presence or absence of increasing concentrations of ligands of formula (I) and formula (II) for histamine-3 receptor competition binding. The binding incubations were conducted in a final volume of 0.5 ml TE buffer at 25° C. and were terminated after 30 minutes. Thioperamide (30 µM) was used to define non-specific binding. All binding reactions were terminated by filtration under vacuum onto polyethylenimine (0.3%) presoaked PERKINELMER UniFilter plates (PERKINELMER is a registered trademark of PerkinElmer, Inc. of Wellesley, Mass.) or WHATMAN GF/B filters (WHATMAN is a registered trademark of Whatman Paper Limited Company of the United Kingdom), followed by three brief washes with 2 ml of ice-cold TE buffer. Bound radiolabel was determined by liquid scintillation counting. For all of the radioligand competition binding assays, $IC_{50}$ values and Hill slopes were determined by Hill transformation of the data and $pK_i$ values were determined by the Cheng-Prusoff equation.

As shown in Table 1, the high $K_i$ values obtained for the compounds of formula (I)) indicate that these compounds do not bind potently to histamine-3 receptors.

TABLE 1

| $Z_1$ | Compound name | $K_i$ (nM)* |
|---|---|---|
| CH | (3aR,5R,6aR)-5-methyl-1-(4'-(6-oxopyridazin-1(6H)-yl)biphenyl-4-yl)octahydropyrrolo[3,4-b]pyrrole 5-oxide | >5000 |
| CH | (3aR,5S,6aR)-5-methyl-1-(4'-(6-oxopyridazin-1(6H)-yl)biphenyl-4-yl)octahydropyrrolo[3,4-b]pyrrole 5-oxide | 2240 |

*Values represent mean of 4 separate determinations.

The compounds of formula (I) are converted, after oral administration or in vivo administration to the compounds of formula (II). Compounds of formula (II) were tested as indicated above for histamine-3 receptor competition binding. As shown in Table 2, compounds of formula (II) have low $K_i$ values. This indicates that compounds of formula (II) are extremely potent as histamine-3 receptors.

TABLE 2

| $Z_2$ | Compound name | $K_i$ (nM) |
|---|---|---|
| CH | 2-(4'-((3aR,6aR)-5-methylhexahydropyrrolo[3,4-b]pyrrol-1(2H)-yl)biphenyl-4-yl)pyridazin-3(2H)-one | 8.2 |
| N | 2-(5-(4-((3aR,6aR)-5-methylhexahydropyrrolo[3,4-b]pyrrol-1(2H)-yl)phenyl)pyridin-2-yl)pyridazin-3(2H)-one | 3.5 |

In vivo Assays in Animal Model

In addition to the utility of in vitro methods for characterizing the histamine-3 binding affinity of compounds, there are animal models of human disease available which demonstrate the utility of compounds of the invention for treating human diseases, conditions or disorders. One animal model of the human disease attention-deficit hyperactivity disorder and related human disorders of attention is an inhibitory avoidance test in SHR rat pups (a Spontaneously Hypertensive strain of rat pups). This model has also been alternatively termed a PAR (passive avoidance response) model. The methodology and utility of this test has been described in the literature, for example in Komater et al., *Psychopharmacology* (Berlin, Germany), Vol. 167(4), pp. 363-372 (2003); Fox et al., "Two Novel and Selective Nonimidazole H3 Receptor Antagonists A-304121 and A-317920: IL In vivo Behavioral and Neurophysiologies Characterization," *Journal of Pharmacology and Experimental Therapeutics*, Vol. 305(3), pp. 897-908 (2003); Cowart et al., *J. Med. Chem.*, Vol. 48, pp. 38-55 (2005); Fox et al., "Pharmacological Properties of ABT-239: IL Neurophysiological Characterization and Broad Preclinical Efficacy in Cognition and Schizophrenia of a Potent and Selective Histamine H3 Receptor Antagonist", *Journal of Pharmacology and Experimental Therapeutics*, Vol. 313, pp. 176-190 (2005); Fox et al., "Effects of Histamine $H_3$ Receptor Ligands GT-2331 and Ciproxifan in a Repeated Acquisition Avoidance Response in the Spontaneously Hypertensive Rat Pup", *Behavioural Brain Research*, Vol. 131 (1,2), pp. 151-161 (2002). In this model, both compounds of formula (II) were active and showed statistically significant beneficial effects after dosing at 0.01-0.03 mg/kg of body weight, when dosed alone by intraperitoneal injection, with behavioral efficacy achieved over a range of plasma concentrations. As prodrugs, compounds of formula (I), when dosed in vivo at 1 mg/kg, produced sustained plasma concentrations of compounds of formula (II) far exceeding levels needed for efficacy, and consequently the preferred doses for compounds of formula (II) range from 0.003-0.1 mg/kg.

In vivo Conversion of Compounds of Formula (I) to Compounds of Formula (II)

Compounds of formula (I) are converted in vivo into compounds of formula (II), therefore compounds of formula (I) can be considered to be prodrugs of compounds of formula (II). This is demonstrated by the following experiments. The pharmacokinetic behavior of a prodrug was evaluated in CD-1 mice, Sprague-Dawley rats, cynomolgus monkeys and beagle dogs.

The prodrug was prepared as a solution in a vehicle of 20% EtOH: 30% propylene glycol in D5W (dextrose 5% in water) at concentrations ranging from 0.1-2 mg/ml. Groups of three rats, dogs or monkeys received a 1 mg/kg (0.5-1 ml/kg) intravenous or oral dose of the example prodrug; additional groups of 30 mice received a 1 mg/kg (10 ml/kg) intravenous or oral dose of the prodrug. The intravenous dose was administered in a jugular (rat), cephalic (dog) or saphenous (monkey) vein; the oral dose was administered by gavage. Serial blood samples were obtained from each animal 0.1 (IV only), 0.25, 0.5, 1, 1.5, 2, 4, 6, 9, 12, 15 (dog only) and 24 hours after dosing. Plasma was separated by centrifugation and stored frozen until analysis.

The plasma concentrations of the administered prodrug and the corresponding histamine-3 receptor ligand were determined by HPLC-MS/MS. The compounds of interest were removed from the plasma using protein precipitation with acetonitrile. Following centrifugation, the supernatant was transferred to a clean container and evaporated to dryness with nitrogen. The prodrug and parent compound were separated from co-extracted contaminant using reverse phase HPLC, with MS/MS detection and quantitation. Spiked standards were analyzed simultaneously with the samples. The plasma drug concentration of each sample was calculated by least squares linear regression analysis (non-weighted) of the peak area ratio (prodrug or parent/internal standard) of the spiked plasma standards versus concentration.

Peak plasma concentrations ($C_{max}$) and the time to peak plasma concentration ($T_{max}$) for both the administered prodrug and the parent drug were read directly from the plasma concentration data for each rat. The plasma concentration data were submitted to multi-exponential curve fitting using WINNONLIN Professional Version 4.0 software (WINNONLIN is a registered trademark of Pharsight Corporation of Palo Alto, Calif.). The characterized prodrug converted to a histamine-3 receptor ligand in all studies. The conversion from the prodrug was measured: complete conversion of the prodrug was observed in the monkey (no prodrug detected); about 50% conversion was noted in rat (prodrug: parent ratio ~1:1) and ~30% conversion in mouse (prodrug: parent ratio ~2:1); conversion was observed in dog (prodrug: parent ratio ~10:1), but less than in monkey, rat, and mouse.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A compound of the formula:

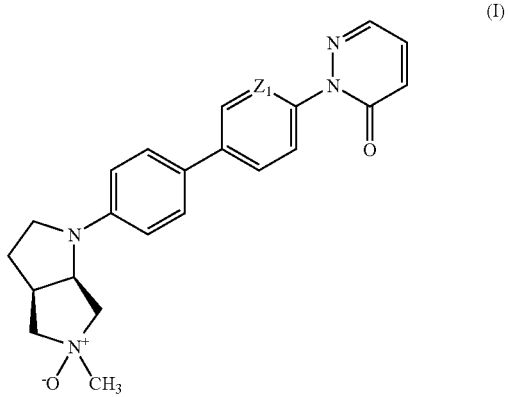

or a pharmaceutically acceptable salt thereof, wherein:
$Z_1$ is N or CH.

2. The compound of claim 1, selected from the group consisting of:
   (3aR,5R,6aR)-5-methyl-1-(4'-(6-oxopyridazin-1(6H)-yl) biphenyl-4-yl) octahydropyrrolo[3,4-b]pyrrole 5-oxide;
   (3aR,5S,6aR)-5-methyl-1-(4'-(6-oxopyridazin-1(6H)-yl) biphenyl-4-yl) octahydropyrrolo[3,4-b]pyrrole 5-oxide;
   (3aR,5R,6aR)-5-methyl-1-(4-(6-(6-oxopyridazin-1(6H)-yl)pyridin-3-yl) phenyl)octahydropyrrolo[3,4-b]pyrrole 5-oxide; and
   (3aR,5S,6aR)-5-methyl-1-(4-(6-(6-oxopyridazin-1(6H)-yl)pyridin-3-yl) phenyl)octahydropyrrolo[3,4-b]pyrrole 5-oxide.

3. A pharmaceutical composition comprising a compound of claim 1 and a pharmaceutically acceptable carrier.

4. A compound that is (3aR,5R,6aR)-5-methyl-1-(4'-(6-oxopyridazin-1(6H)-yl)biphenyl-4-yl)octahydropyrrolo[3,4-b]pyrrole 5-oxide.

5. A compound that is (3aR,5S,6aR)-5-methyl-1-(4'-(6-oxopyridazin-1(6H)-yl)biphenyl-4-yl)octahydropyrrolo[3,4-b]pyrrole 5-oxide.

6. A compound that is (3aR,5R,6aR)-5-methyl-1-(4-(6-(6-oxopyridazin-1(6H)-yl)pyridin-3-yl)phenyl)octahydropyrrolo[3,4-b]pyrrole 5-oxide.

7. A compound that is (3aR,5S,6aR)-5-methyl-1-(4-(6-(6-oxopyridazin-1(6H)-yl)pyridin-3-yl)phenyl)octahydropyrrolo[3,4-b]pyrrole 5-oxide.

* * * * *